United States Patent
Kageyama et al.

(10) Patent No.: US 9,345,243 B2
(45) Date of Patent: *May 24, 2016

(54) CHEMICALS COMPOSITION FOR REDUCING STRESS ON PLANT

(71) Applicants: Nippon Soda Co., Ltd., Chiyoda-ku, Tokyo (JP); Shizuoka Prefecture, Shizuoka-shi, Shizuoka (JP)

(72) Inventors: Chizuko Kageyama, Iwata (JP); Hiroyuki Iyozumi, Iwata (JP); Hideki Nukui, Iwata (JP); Kimihiko Kato, Shizuoka (JP); Junya Mannen, Shizuoka (JP); Kazuyuki Tomida, Odawara (JP); Shinsuke Sano, Odawara (JP); Hideki Kato, Odawara (JP); Satoru Makita, Odawara (JP); Toshio Mizuno, Makinohara (JP)

(73) Assignees: Nippon Soda Co., Ltd., Tokyo (JP); Shizuoka Prefecture, Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/415,292

(22) PCT Filed: Jul. 19, 2013

(86) PCT No.: PCT/JP2013/004429
§ 371 (c)(1),
(2) Date: Jan. 16, 2015

(87) PCT Pub. No.: WO2014/013743
PCT Pub. Date: Jan. 23, 2014

(65) Prior Publication Data
US 2015/0164072 A1 Jun. 18, 2015

(30) Foreign Application Priority Data
Jul. 20, 2012 (JP) .................................. 2012-161897

(51) Int. Cl.
*A01N 43/08* (2006.01)

(52) U.S. Cl.
CPC .................. *A01N 43/08* (2013.01)

(58) Field of Classification Search
CPC .............................. A01N 43/08; A01N 25/32
USPC .................................................. 514/532, 474
See application file for complete search history.

(56) References Cited

U.S. PATENT DOCUMENTS

| 4,567,161 A | 1/1986 | Posanski et al. |
| 6,420,419 B1 | 7/2002 | Suzuki et al. |
| 6,458,745 B1 | 10/2002 | Runge et al. |
| 2005/0031744 A1 | 2/2005 | Paliyath et al. |
| 2007/0104750 A1 | 5/2007 | Wilson et al. |
| 2008/0274888 A1 | 11/2008 | Goldstein |
| 2012/0004104 A1 | 1/2012 | Casaña Giner et al. |
| 2012/0172580 A1 | 7/2012 | Masuta et al. |
| 2012/0283104 A1 | 11/2012 | Jung et al. |
| 2014/0364310 A1 | 12/2014 | Li et al. |
| 2015/0126368 A1* | 5/2015 | Kageyama ............ A01N 43/08 504/128 |

FOREIGN PATENT DOCUMENTS

| CN | 101766217 A | 7/2010 |
| CN | 102349513 A | 2/2012 |
| CN | 102584482 A | 7/2012 |
| EP | 0875514 A1 | 11/1998 |
| EP | 2174546 A1 | 4/2010 |
| EP | 2747540 A2 | 7/2014 |
| JP | 04-342507 A | 11/1992 |
| JP | 2008-538566 A | 10/2008 |
| WO | WO 00/10390 A1 | 3/2000 |
| WO | WO 2006/050141 A1 | 5/2006 |
| WO | WO 2009/013373 A1 | 1/2009 |
| WO | WO 2011/030816 A1 | 3/2011 |
| WO | WO 2011/064312 A1 | 6/2011 |
| WO | WO 2013/028795 A2 | 2/2013 |
| WO | WO 2013/093578 A1 | 6/2013 |

(Continued)

OTHER PUBLICATIONS

FRAC and the EPA Office of Pesticide Program(www.epagov/oppmsd1/PR Notices/pr2001-5.pdf) p. 4.*
Miyamoto et al., "Effect of Ascorbic Acid Supply on the Response of *Nicotiana rustica* Plants to Tobacco Mosaic Virus Infection," Ann. Phytopath. Soc. Japan, 1980, 46(3):361-363.

* cited by examiner

*Primary Examiner* — T. Victor Oh
(74) *Attorney, Agent, or Firm* — Foley & Lardner LLP

(57) ABSTRACT

A chemical composition for reducing stress on a plant comprising: at least one substance (A) selected from the group consisting of compounds represented by Formula (I) and the like and a salt thereof; and a substance (B) which affects a physiological function of the plant [in Formula (I), $R^1$ to $R^4$ each independently represents a hydrogen atom, $-SO_3H$, $-PO_3H_2$, glycosyl group or $-COR^{11}$. $R^{11}$ represents an unsubstituted or substituted C1 to C30 alkyl group or an unsubstituted or substituted C2 to C30 alkenyl group.].

(I)

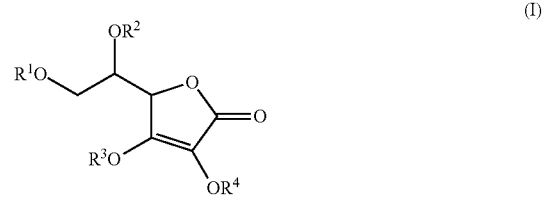

7 Claims, No Drawings

CHEMICALS COMPOSITION FOR REDUCING STRESS ON PLANT

CROSS-REFERENCE TO RELATED APPLICATIONS

This application is a National Stage application of PCT/JP2013/004429, filed Jul. 19, 2013, which claims priority from Japanese application no. 2012-161897, filed Jul. 20, 2012.

TECHNICAL FIELD

The present invention relates to a chemicals composition for reducing stress on a plant. More specifically, the present invention relates to a chemicals composition for reducing biological stress, physical stress, or chemical stress which affects the growth of a plant.

BACKGROUND ART

Plants grown at farmlands or ordinary home gardens are always exposed to various biological or non-biological stresses. In general, agricultural crops subjected to breed improvement tend to be less resistant to these stresses. In order to reduce biological stress such as agricultural pests and weeds to maintain a crop yield, agricultural chemicals are used such as fungicides, insecticides and herbicides. However, agricultural chemicals may have insufficient effects, and may cause phytotoxicity when improperly used, and may allow agricultural pests and weeds to develop resistance to the agricultural chemicals, and may pose concerns about safety for environmental life. Meanwhile, the right plant in the right place, breed improvement, irrigation, greenhouse, soil improvement and the like are utilized to respond environmental stress such as temperature, moisture, illuminance, soil pH and salt concentration. Attempts have been made for conferring stress resistance using a plant growth regulator and the like, but effects have been unsatisfactory. Further, plant viral diseases may cause serious damage to key crops such as cereal crops, vegetables and fruit trees. However, to date, agricultural chemicals have not been found which sufficiently demonstrate practical effects against plant viral diseases.

Meanwhile, Non-patent Literature 1 describes that ascorbic acid is involved in disease resistance, hormone actions and the like, and Non-patent Literature 2 describes that ascorbic acid affects plant aging. However, even when ascorbic acid is externally given to a plant, its physiological effect is very limited because ascorbic acid is present at a high concentration in a plant body. Therefore, there will be almost no practical effect.

Nonetheless, Patent Literature 1 describes that a certain derivative of ascorbic acid demonstrates a preventive and curative effect against a plant virus disease, and proposes to apply it to a plant. Further, Patent Literature 2 discloses a composition comprising an antimicrobic antibiotic such as neomycin sulfate, and ascorbic acid, and states that this composition can control a plant disease. Moreover, for purposes such as the stabilization of an agrochemically active ingredient (Patent Literature 3) and controlled release (Patent Literature 4), examples have been proposed in which ascorbic acid is used in combination with an agricultural chemical.

CITATION LIST

Non-Patent Literatures

Non-patent Literature 1: Vitamins 79 (2): 116-117 (2005)
Non-patent Literature 2: The Horticulture Journal, 6 (2): 169-175

Patent Literatures

Patent Literature 1: WO 2011/030816 A
Patent Literature 2: JP 2001-508808 A
Patent Literature 3: JP 2001-342102 A
Patent Literature 4: JP 2010-168298 A

SUMMARY OF THE INVENTION

Problems to be Solved by the Invention

An object of the present invention is to provide a chemicals composition for reducing biological stress, physical stress or chemical stress which affects the growth of a plant.

Means for Solving the Problems

As a result of conducting extensive studies to achieve the above object, the present inventors complete the present invention which includes the following aspects.

[1] A chemicals composition for reducing stress on a plant, wherein the composition comprises at least one substance (A) selected from the group consisting of compounds represented by Formula (I), compounds represented by Formula (II) and salts thereof, and a substance (B) which affects a physiological function of the plant.

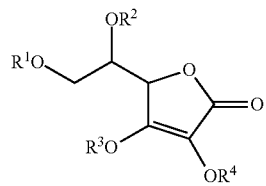

(I)

[in Formula (I), $R^1$ to $R^4$ each independently represents a hydrogen atom, $-SO_3H$, $-PO_3H_2$, a glycosyl group or $-COR^{11}$. $R^{11}$ represents an unsubstituted or substituted C1 to C30 alkyl group or an unsubstituted or substituted C2 to C30 alkenyl group.]

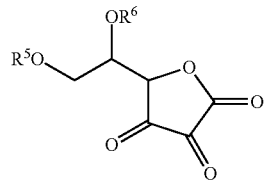

(II)

[in Formula (II), $R^5$ and $R^6$ each independently represents a hydrogen atom, $-SO_3H$, $-PO_3H_2$, a glycosyl group or $-COR^{11}$. $R^{11}$ represents an unsubstituted or substituted C1 to C30 alkyl group or an unsubstituted or substituted C2 to C30 alkenyl group.]

[2] The composition according to [1], wherein the substance (B) is at least one selected from the group consisting of fungicides, insecticides, plant growth regulators and herbicides.

[3] The composition according to [1], wherein the substance (B) is a respiratory inhibitor.

[4] The composition according to [1], wherein the substance (B) is a strobilurin compound.

[5] The composition according to [1], wherein the substance (A) is a compound represented by Formula (I) [provided that $R^1$ to $R^4$ are each not simultaneously a hydrogen atom] or a salt thereof.

[6] The composition according to [1], wherein the substance (A) is a compound represented by Formula (I) [provided that at least one of $R^1$ to $R^4$ represents $-COR^{11}$, and $R^{11}$ represents an unsubstituted or substituted C12 to C30 alkyl group or an unsubstituted or substituted C12 to C30 alkenyl group.] or a salt thereof.

[7] The composition according to [1], wherein the substance (A) is a compound represented by Formula (I) [provided that $R^1$ to $R^4$ each independently represent a hydrogen atom or $-COR^{11}$, and at least one of $R^1$ to $R^4$ represent $-COR^{11}$. $R^{11}$ represents an unsubstituted or substituted C1 to C30 alkyl group or an unsubstituted or substituted C2 to C30 alkenyl group. $R^{11}$ in at least one of $-COR^{11}$ represents an unsubstituted or substituted C12 to C30 alkyl group or an unsubstituted or substituted C12 to C30 alkenyl group.] or a salt thereof.

[8] A method of reducing stress on a plant, wherein the method comprises applying the composition according to any one of the aforementioned [1] to [7] to the plant.

[9] The method according to [8], wherein the stress is at least one of biological stress due to plant viruses, phytopathogenic bacteria, phytopathogenic filamentous fungi, agricultural pests or weeds: or physical or chemical stress due to high temperature, low temperature, high illuminance, low illuminance, excessive humidity, dryness, salinity, acidity, agricultural chemicals, chemical substances or heavy metals.

Advantageous Effects of the Invention

The composition according to the present invention has an effect in which resistance against biological stress, physical stress, or chemical stress which affects the growth of a plant is conferred on a plant. Since the resistance of a plant to stress is increased when the composition according to the present invention is applied to the plant, for example, phytotoxicity due to an agricultural chemical containing a substance which affects a physiological function of the plant and the like may be reduced, and damage due to plant diseases including virus diseases may be reduced. Moreover, even under poor environmental conditions such as high temperature, low temperature, dryness and soil conditions, reduction in crop yields, deterioration of the quality and the like can be prevented.

EMBODIMENTS FOR CARRYING OUT THE INVENTION

The chemicals composition for reducing stress on a plant according to the present invention comprises the substance (A) and the substance (B) which affects a physiological function of the plant.

(Substance (A))

The substance (A) is at least one selected from the group consisting of compounds represented by Formula (I), compounds represented by Formula (II) and salts thereof.

In Formula (I), $R^1$ to $R^4$ each independently represents a hydrogen atom, $-SO_3H$, $-PO_3H_2$, a glycosyl group or $-COR^{11}$.

In Formula (II), $R^5$ and $R^6$ each independently represents a hydrogen atom, $-SO_3H$, $-PO_3H_2$, a glycosyl group or $-COR^{11}$.

The glycosyl group is a sugar residue such as a monosaccharide or a low molecular weight oligosaccharide (which is, specifically, a partial structure of a molecule in which a hemiacetal hydroxy group at a sugar portion is removed to give a connecting position). Examples of monosaccharides include glucose, galactose, fructose, rhamnose and the like, and examples of oligosaccharides include rutinose, vicianose, lactose, maltose, sucrose and the like. Therefore, examples of glycosyl groups include a glucosyl group, a galactosyl group, a fructosyl group, a rhamnosyl group and the like. Further, glycosyl groups include disaccharide groups in which any combination of these groups are connected in the 1→2 linkage, the 1→3 linkage, the 1→4 linkage or the 1→6 linkage.

$R^{11}$ in $-COR^{11}$ represents an unsubstituted or substituted C1 to C30 alkyl group or an unsubstituted or substituted C2 to C30 alkenyl group.

As used herein, the term "unsubstituted" means that a corresponding group comprises only a group serving as a mother nucleus. Note that when described only under the name of a group serving as a mother nucleus without a description of "substituted", it means "unsubstituted" unless otherwise stated.

Meanwhile, the term "substituted" means that any hydrogen atom in a group serving as a mother nucleus is substituted with a group having a structure which is different from or the same as the mother nucleus. Therefore, the term "substituent" is another group substituted on a group serving as a mother nucleus. The number of substituents may be 1, or may be 2 or more. Two or more substituents may be the same, or may be different. For example, a substituted C1 to C30 alkyl group is a group having a structure in which the group serving as a mother nucleus is a C1 to C30 alkyl group, and any hydrogen atom thereof is substituted with a group having a different structure ("substituent").

A "C1 to C30 alkyl group" in $R^{11}$ is a saturated hydrocarbon group comprising 1 to 30 carbon atoms. A C1 to C30 alkyl group may be a linear chain, or may be a branched chain. Examples of C1 to C30 alkyl groups include a methyl group, an ethyl group, an n-propyl group, an n-butyl group, an n-pentyl group, an n-hexyl group, an n-heptyl group, an n-octyl group, an i-propyl group, an i-butyl group, an s-butyl group, a t-butyl group, an i-pentyl group, a neopentyl group, a 2-methylbutyl group, a 2,2-dimethylpropyl group, an i-hexyl group, a heptyl group, an octyl group, a nonyl group, a decyl group, an undecyl group, a dodecyl group, a tridecyl group, a tetradecyl group (a myristyl group), a pentadecyl group, a hexadecyl group (a cetyl group, a palmityl group), a heptadecyl group, an octadecyl group (a stearyl group), a nonadecyl group, an icosyl group, a henicosyl group, a triacontyl group and the like.

A "C2 to C30 alkenyl group" in $R^{11}$ is an unsaturated hydrocarbon group comprising 2 to 30 carbon atoms having at least one carbon-carbon double bond. A C2 to C30 alkenyl group may be a linear chain, or may be a branched chain. Examples of C2 to C30 alkenyl groups include a vinyl group, a 1-propenyl group, an isopropenyl group, an allyl group, a 1-butenyl group, a 2-butenyl group, a 3-butenyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group, a 5-hexenyl group, a 1-heptenyl group, a 6-heptenyl group, a 1-octenyl group, a 7-octenyl group, a 1-methyl-allyl group, a 2-methyl-allyl group, a 1-methyl-2-butenyl group, a 2-methyl-2-butenyl group, an octenyl group, a nonenyl group, a decenyl group, an undecenyl group, a dodecenyl group, a tridecenyl group, a tetradecenyl group, a pentadecenyl group, a hexadecenyl group, a heptadecenyl group, an octadecenyl group, a nonadecenyl group, an icosenyl group, a henicosenyl group, a triacontenyl group and the like.

Examples of groups which can be a "substituent" in the C1 to C30 alkyl group or the C2 to C30 alkenyl group include a hydroxyl group; a mercapto group; an amino group; a nitro group; a halogen atom such as a chlorine atom, a fluorine atom, a bromine atom; an alkoxy group such as a methoxy group, an ethoxy group, an isopropoxy group, an n-propoxy group, an n-butoxy group, an isobutoxy group, an s-butoxy group, a t-butoxy group; an aryloxy group such as a phenoxy group, a 1-naphthyloxy group; a haloalkoxy group such as a fluoromethoxy group, a difluoromethoxy group, a trifluoromethoxy group, a 2-chloroethoxy group, a 2,2,2-trichloroethoxy group, a 1,1,1,3,3,3-hexafluoro-2-propoxy group; an alkylthio group such as a methylthio group, an ethylthio group; an arylthio group such as a phenylthio group, a 1-naphthylthio group; an alkylamino group such as a methylamino group, a diethylamino group; an arylamino group such as an anilino group, a 1-naphthyl amino group; a cyano group and the like.

Preferably, the above $R^{11}$ represents an unsubstituted or substituted C8 to C20 alkyl group or an unsubstituted or substituted C8 to C20 alkenyl group.

The substance (A) is preferably a compound represented by Formula (I) or a salt thereof. Further, preferably, $R^1$ to $R^4$ in Formula (I) are not simultaneously hydrogen atoms.

Moreover, the substance (A) is preferably a compound represented by Formula (I) [at least one of $R^1$ to $R^4$ represents —$COR^{11}$. $R^{11}$ represents an unsubstituted or substituted C12 to C30 alkyl group or an unsubstituted or substituted C12 to C30 alkenyl group.] or a salt thereof.

Examples of "C12 to C30 alkyl groups" include a dodecyl group, a tridecyl group, a tetradecyl group (a myristyl group), a pentadecyl group, a hexadecyl group (a cetyl group, a palmityl group), a heptadecyl group, an octadecyl group (a stearyl group), a nonadecyl group, an icosyl group, a henicosyl group, a triacontyl group and the like.

Examples of "Substituted C12 to C30 alkyl groups" include a 2-hydroxytridecyl group, a 1-hydroxypentadecyl group, an 11-hydroxyheptadecyl group, a 1-aminoheptadecyl group and the like.

Examples of "C12 to C30 alkenyl groups" include a dodecenyl group, a tridecenyl group, a tetradecenyl group, a pentadecenyl group, a hexadecenyl group, a heptadecenyl group, an octadecenyl group, a nonadecenyl group, an icosenyl group, a henicosenyl group, a triacontenyl group and the like.

Examples of "substituted C12 to C30 alkenyl groups" include a 7-hydroxy-8-pentadecenyl group, a 1-hydroxy-8-heptadecenyl group, a 1-amino-8-heptadecenyl group and the like.

Further, the substance (A) is preferably a compound represented by Formula (I) [$R^1$ to $R^4$ each independently represents a hydrogen atom or —$COR^{11}$, and at least one of $R^1$ to $R^4$ represents —$COR^{11}$, and $R^{11}$ represents an unsubstituted or substituted C1 to C30 alkyl group or an unsubstituted or substituted C2 to C30 alkenyl group, and $R^{11}$ in at least one of —$COR^{11}$ represents an unsubstituted or substituted C12 to C30 alkyl group or an unsubstituted or substituted C12 to C30 alkenyl group.] or a salt thereof.

Specific examples of the substance (A) as described above can include ascorbic acid 6-myristate, ascorbic acid 6-palmitate, ascorbic acid 6-stearate, ascorbic acid 2-myristate, ascorbic acid 2-palmitate, ascorbic acid 2-stearate, ascorbic acid 2,6-dimyristate, ascorbic acid 2,6-dipalmitate, ascorbic acid 2,6-distearate and the like.

There is no particular limitation for salts of a compound represented by Formula (I) and salts of a compound represented by Formula (II) as long as they are agriculturally and horticulturally acceptable salts. They can include, for example, an alkali metal salt such as a sodium salt, a potassium salt; an alkaline earth metal salt such as a calcium salt, a magnesium salt and the like.

The substance (A) used for the present invention can be obtained by a known synthesis approach. For example, an esterification reaction of a fatty acid compound with ascorbic acid for introducing —$COR^{11}$ into any of $R^1$ to $R^4$, an esterification reaction of a phosphoric acid compound with ascorbic acid for introducing —$PO_3H_2$ into any of $R^1$ to $R^4$, an esterification reaction of a sulfuric acid compound with ascorbic acid for introducing —$SO_3H$ into any of $R^1$ to $R^4$ and other known reactions can be used for synthesis. Further, the substance (A) obtained by the aforementioned synthesis method can be purified by a known method such as extraction, distillation, chromatography. Moreover, many of the substances (A) used for the present invention are commercially available, and therefore it is also possible to use them.

The structure of the substance (A) can be identified or confirmed by a known analytical means such as an IR spectrum, an NMR spectrum, a mass spectrum, elementary analysis.

The substance (A) may be used alone, but is preferably used in combination of at least two. In a case where a combination of two is used, the substance (A) is preferably a composition comprising a water soluble substance (A1) of those selected from the group consisting of compounds represented by Formula (I), compounds represented by Formula (II) and salts thereof; and a lipid soluble substance (A2) of those selected from the group consisting of compounds represented by Formula (I), compounds represented by Formula (II) and salts thereof, because an effect of the substance (A) is synergistically enhanced.

In a case where a combination of two is used, more specifically, the substance (A) is preferably a composition comprising at least one water soluble substance (A1) selected from the group consisting of compounds represented by Formula (Ia), compounds represented by Formula (IIa) and salts thereof; and at least one lipid soluble substance (A2) selected from the group consisting of compounds represented by Formula (Ib), compounds represented by Formula (IIb) and salts thereof.

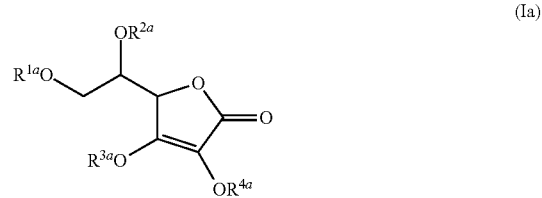

(Ia)

[In Formula (Ia), $R^{1a}$ to $R^{4a}$ each independently represents a hydrogen atom, —$SO_3H$, —$PO_3H_2$ or a glycosyl group.]

(IIa)

[In Formula (IIa), $R^{5a}$ to $R^{6a}$ each independently represents a hydrogen atom, —$SO_3H$, —$PO_3H_2$ or a glycosyl group.]

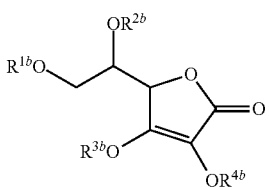

(Ib)

[In Formula (Ib), $R^{1b}$ to $R^{4b}$ each independently represents a hydrogen atom or —$COR^{11}$. At least one of $R^{1b}$ to $R^{4b}$ represents —$COR^{11}$, and $R^{11}$ represents an unsubstituted or substituted C1 to C30 alkyl group or an unsubstituted or substituted C2 to C30 alkenyl group, preferably an unsubstituted or substituted C12 to C30 alkyl group or an unsubstituted or substituted C12 to C30 alkenyl group.]

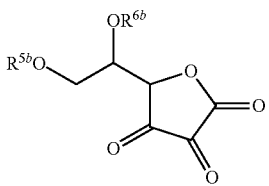

(IIb)

[In Formula (IIb), $R^{5b}$ and $R^{6b}$ each independently represents a hydrogen atom or —$COR^{11}$. At least one of $R^{5b}$ and $R^{6b}$ represents —$COR^{11}$, and $R^{11}$ represents an unsubstituted or substituted C1 to C30 alkyl group or an unsubstituted or substituted C2 to C30 alkenyl group, preferably an unsubstituted or substituted C12 to C30 alkyl group or an unsubstituted or substituted C12 to C30 alkenyl group.]

The mass ratio of the lipid soluble substance (A2) to the water soluble substance (A1) is usually from 0.001 to 1000, preferably from 0.1 to 10.

(Substance (B))

Examples of the substance (B) which affects a physiological function of a plant used for the present invention include herbicides; growth regulators; plant hormones; resistance inducers against a pathogen; fungicides, insecticides, miticides, repellents, microbial agricultural chemicals, fertilizers, surfactants which show phytotoxicity when used at a high concentration; and the like. Among these, preferred is at least one selected from the group consisting of fungicides, insecticides, plant growth regulators and herbicides. Further, the substance (B) is preferably a respiratory inhibitor. Furthermore, the substance (B) is preferably strobilurin compounds.

Examples of fungicides include those such as captan, folpet, thiuram, dilam, zineb, maneb, mancozeb, propineb, polycarbamate, chlorothalonil, quintozene, captaphore, iprodione, procymidone, fluoroimide, mepronil, flutolanil, pencycuron, oxycarboxin, fosetylaluminium, propamocarb, hexaconazole, imibenconazole, tebuconazole, difenoconazole, prothioconazole, fenbuconazole, diclobutrazol, bitertanol, myclobutanil, flusilazole, hexaconazole, etaconazole, fluotrimazole, triadimefon, triadimenol, flutriafen, penconazole, diniconazole, cyproconazole, fenarimol, triflumizole, prochloraz, imazalil, kresoxim-methyl, trifloxystrobin, azoxystrobin, pyraclostrobin, orysastrobin, pefurazoate, tridemorph, fenpropimorph, trifolin, buthiobate, pyrifenox, anilazine, polyoxin, metalaxyl, oxadixyl, furalaxyl, isoprothiolane, probenazole, pyrrolnitrin, blasticidin S, kasugamycin, validamycin, dihydrostreptomycin sulfate, benomyl, carbendazim, thiophanate-methyl, hymexazol, basic copper chloride, basic copper sulfate, fentinacetate, triphenyltin hydroxide, diethofencarb, chinomethionate, binapacryl, lecithin, sodium bicarbonate, dithianon, dinocap, fenaminosulf, dichlomedin, guazatine, dodine, IBP, edifenphos, mepanipyrim, ferimzone, trichlamid, metasulfocarb, fluazinam, etoquinolak, dimethomorph, pyroquilon, tecloftalam, fthalide, phenazine oxide, thiabendazole, tricyclazole, vincrozoline, cymoxanil, guazatine, propamocarb hydrochloride, oxolinic acid, cyflufenamid, iminoctadine, triazine, fenhexamid, cyazofamid, cyprodinil, carpropamide, boscalid; and also include resistance inducers against a pathogen such as probenazole, tiadinil.

Among these, particularly preferred are strobilurin based fungicides such as kresoxim-methyl, trifloxystrobin, azoxystrobin, pyraclostrobin, orysastrobin.

Examples of herbicides include 2,4-D, MCPA, clomeprop, dicamba, chlorotoluron, diuron, linuron, isouron, fenuron, neburon, simazine, atrazine, simetryn, prometryn, hexazinone, propazine, desmetryn, terbumeton, propanil, bromoxynil, ioxynil, pyridate, chloridazon, bentazone, chlomethoxyfen, bifenox, acifluorfen sodium salt, flumioxazin, thidiazimin, oxadiazon, sulfentrazone, pentoxazone, pyraclonil, pyrazolynate, pyrazoxyfen, benzofenap, mesotrione, isoxaflutole, isoxachlortole, amitrole, aclonifen, diflufenican, benzobicyclon, diclofop-methyl, fluazifop-butyl, alloxydim sodium salt, clethodim, sethoxydim, tralkoxydim, tepraloxydim, bensulfuron-methyl, pyrazosulfuron-ethyl, rimsulfuron, imazosulfuron, prosulfuron, flumetsulam, diclosulam, metosulam, imazapyr, imazaquin, pyrithiobac-sodium salt, bispyribac-sodium salt, pyriminobac-methyl, flucarbazone, propoxycarbazone, glyphosate, glyphosate ammonium salt, glufosinate, trifluralin, pendimethalin, benfluralin, prodiamine, propham, dithiopyr, alachlor, metolachlor, pethoxamid, acetochlor, propachlor, dimethenamid, diphenamid, napropamide, mefenacet, fentrazamide, molinate, dimepiperate, cycloate, esprocarb, thiobencarb, thiocarbazil, bensulide, dalapon, asulam, DNOC, dinoseb, flupoxam, traiziflam, quinchlorac, cinmethylin, dazomet, dymron, etobenzanide, oxaziclomefone, pyributicarband the like.

Examples of insecticides include organophosphate based and carbamate based insecticides such as fenthion, fenitrothion, diazinon, chlorpyrifos, ESP, vamidothion, phenthoate, dimethoate, formothion, malathion trichlorfon, thiometon, phosmet, dichlorvos, acephate, EPBP, methylparathion, oxydemeton-methyl, ethion, salithion, cyanophos, isoxathion, pyridaphenthion, phosalone, methidathion, sulprofos, chlorfenvinphos, tetrachlorvinphos, dimethylvinphos, propaphos, isofenphos, ethylthiometon, prophenophos, pyraclophos, monocrotophos, azinephosmethyl, aldicarb, methomyl, thiodicarb, carbofuran, carbosulfane, benfuracarb, furathiocarb, propoxur, BPMC, MTMC, MIPC, carbaryl, pirimicarb, ethiofencarb, phenoxycarb, cartap, thiocyclam, bensultap; pyrethroid based insecticides such as permethrin, cypermethrin, deltamethrin, fenvalerate, fenpropathrin, pyrethrin, allethrin, tetramethrin, resmethrin, dimethrin, propathrin, phenothrin, prothrin, fluvalinate, cyfluthrin, cyhalothrin, flucythrinate, etofenprox, cycloprothrin, tralomethrin, silafluofen, acrinathrin; neonicotinoid based insecticides such as imidacloprid, acetamiprid, nitenpyram, thiacloprid, clothianidin, thiamethoxam, dinotefuran, nithiazine; benzoylphenylurea based insecticides such as diflubenzuron, chlorfluazuron, hexaflumuron, triflumuron, flufenoxuron, furcycloxuron, buprofezin, pyriproxifen, methoprene, benzoepin, diafenthiuron, fipronil, nicotine sulfate, rotenone, metaldehyde, acetamiprid, chlorphenapyl, nitenpyram, thiacloprid, clothianidin, thiamethoxam, dinotefuran, indoxacarb, pymetrozine, spinosad, emamectin, pyridalyl, tebufenozide, chromafenozide, methoxyfenozide, tolfenpyrad, flubendiamide, chlorantraniliprole, cyantraniliprole; nematicides such as fenamiphos, phosthiazate, cadusafos; miticides such as chlorbenzilate, phenisobromolate, dicofol, amitraz, BPPS, benzomate, hexythiazox, fenbutatin-oxide, polynactin, chinomethionate, CPCBS, tetradifon, avermectin, milbemectin, clofentezine, cyhexatin, pyridaben, fenpyroximate, tebufenpyrad, cyenopyrafen, cyflumetofen, pyrimidifen, phenothiocarb, dienochlor, fluacrypyrim, acequinocyl, bifenazate, etoxazole, spirodiclofen, fenazaquin; microorganism-derived formulations such as BT agents; and the like.

Among these, particularly preferred are neonicotinoid based insecticides such as imidacloprid, acetamiprid, nitenpyram, thiacloprid, clothianidin, thiamethoxam, dinotefuran, nithiazine; and insecticides or miticides which have respiratory inhibition effects such as chlorphenapyl, pymetrozine, pyridaben, fenpyroximate, tolfenpyrad, tebufenpyrad, cyenopyrafen, cyflumetofen, fluacrypyrim, acequinocyl, fenazaquin.

Examples of plant hormones include gibberellins (for example, gibberellin A3, gibberellin A4, gibberellin A7 and the like), auxins (for example, 2,4-D, IAA, NAA and the like), cytokinins (for example, kinetin, benzyladenine and the like), abscisic acid, jasmone acids, brassinosteroids, strigolactones, salicylic acid and the like.

As plant growth regulators, in addition to the aforementioned plant hormones, mentioned are hymexazol, uniconazole, trinexapac, daminozide, cyanamide and the like.

Examples of fertilizers include nitrogenous fertilizers, phosphatic fertilizers, potash fertilizers, calcareous fertilizers, magnesium fertilizers, silicate fertilizers, trace element fertilizers, animal matter fertilizers, plant matter fertilizers and the like. When the concentration of a water-soluble component of a fertilizer is too high, fertilizer disorders such as withering and death of root and leaf may be caused to a plant. Further, when a certain type of a fertilizer such as ammonium sulfate is used in a large amount, the growth of a plant may be compromised through soil acidification.

A surfactant is used as an auxiliary component of an agrochemical formulation, as an active component of some insecticides or miticides, or as a spreader. Examples of surfactants include nonionic surfactants such alkylphenyl ether in which polyoxyethylene is added, alkyl ether in which polyoxyethylene is added, higher fatty acid ester in which polyoxyethylene is added, sorbitan higher fatty acid ester in which polyoxyethylene is added, tristyrylphenyl ether in which polyoxyethylene added; anionic surfactants such as a sulfuric ester salt of alkylphenyl ether in which polyoxyethylene is added, alkylbenzene sulfonate, a sulfuric ester salt of higher alcohol, alkylnaphthalenesulfonate, polycarboxylate, lignin sulfonate, a formaldehyde condensate of alkylnaphthalenesulfonate, a copolymer of isobutylene-maleic anhydride; cationic surfactants such as alkyltrimethylammonium chloride, methyl•polyoxyethylene•alkylammonium chloride, alkyl•N-methylpyridium bromide, mono- or di-alkylmethylated ammonium chloride, alkylpentamethylpropylenediamine dichloride, alkyldimethylbenzalkonium chloride, benzethonium chloride; amphoteric surfactants such as dialkyldiaminoethylbetaine, alkyldimethylbenzylbetaine, dialkyldiaminoethylglycine, alkyldimethylbenzylglycine; and the like.

The chemicals composition according to the present invention can be obtained by mixing the substance (A) with the substance (B) by a known method. The mass ratio of the substance (B) to the substance (A) is usually from 0.0001 to 100, preferably from 0.001 to 100, more preferably from 0.01 to 10.

Further, the chemicals composition according to the present invention can be prepared into a formulation such as a wettable powder, an emulsifiable concentrate, a water soluble powder, a water dispersible granule, a dust, a tablet and the like. There is no particular limitation for a method of preparing a formulation, and a known preparation method can be used depending on a dosage form.

There is no particular limitation for a method of applying the chemicals composition according to the present invention to a plant, and a known application method in the field of agriculture and horticulture can be used. Further, an application method to a plant can be suitably determined depending on the type and the like of the target plant. For example, preferred modes of application include foliage application, dipping treatment, soil irrigation, seed treatment, water culture medium treatment, smoking treatment, ordinary temperature fogging treatment and the like. The chemicals composition according to the present invention may be used without limitation by cultivation forms such as soil cultivation and hydroponic cultivation. Further, excellent effects can be achieved even when used in a special environment such as meristem culture. An application amount of the chemicals composition according to the present invention can be suitably determined depending on meteorological conditions, formulation forms, application times, application methods, application places, target disease to be controlled, target crops and the like.

There is no particular limitation for plants to which the chemicals composition according to the present invention may be applied, and they may be either edible plants or non-edible plants. Examples of the target plants include cereal crops such as rice, wheat, corn; legumes such as soybean, azuki bean), peanut; fruit trees such as citrus, apple, pear, grape, peach; vegetables such as tomato, lettuce, cabbage, onion, green onion, bell pepper; pepos such as cucumber, watermelon, melon, pumpkin; root vegetables such as potato, sweet potato, Chinese yam, carrot, radish; crops for processing such as cotton, sugarbeet, hop, sugarcane, rubber tree, coffee, tobacco, tea; grass such as ryegrass, timothy, orchard grass; lawn grasses such as bentgrass, Zoysia grass.

Stresses targeted by the chemicals composition according to the present invention include biological stress due to plant viruses, phytopathogenic bacteria, phytopathogenic filamentous fungi, agricultural pests or weeds; physical or chemical stress due to high temperature, low temperature, high illuminance, low illuminance, excessive humidity, dryness, salinity, acidity, agricultural chemicals, chemical substances or heavy metals.

There is no particular limitation for plant viruses which may cause stress. For example, they preferably can include gemini viruses having a single stranded DNA as the genome, cauliflower mosaic virus having double stranded DNA as the genome, tobacco mosaic virus, tomato bushy stunt virus having a single stranded RNA as the genome, rice ragged stunt virus having double stranded RNA as the genome and the like.

There is no particular limitation for phytopathogenic bacteria which may cause stress. For example, they include *Burkholderia plantarii, Acidovorax avenae, Burkholderia glumae, Xanthomonas campestris* pv. *oryzae, Pseudomonas lachrymans, Erwinia carotovora* and the like.

There is no particular limitation for phytopathogenic filamentous fungi which may cause stress. For example, they include *Pyricularia oryzae, Gibberella fujikuroi, Cochliobolus miyabeanus, Erysiphe graminis* f.sp. *tritici, Gibberella zeae, Puccinia recondita, Septoria tritici, Leptosphaeria nodorum, Ustilago tritici, Sphaerotheca fuliginea, Pseudoperonospora cubensis, Mycosphaerella melonis, Fusarium oxysporum, Botrytis cinerea, Colletotrichum orbiculare, Cladosporium cucumerinum, Corynespora cassicola, Cladosporium fulvum, Phytophthora infestans* and the like.

There is no particular limitation for agricultural pests which may cause stress, and example of the pests include:

Lepidoptera pests, for example, *Spodoptera frugiperda, Leucania, Spodoptera litura, Agrotis ipsilon, Adoxophyes honmai, Homona magnanima, Carposina niponensis Walsingham, Cydia molesta, Phyllocnistis citrella, Caloptilia theivora, Phyllonorycter ringoniella, Lymantria dispar, Euproctis pseudoconspersa, Chilo suppressalis, Cnaphalocrocis medinalis, Ostrinia nubilalis, Hyphantria cunea, Cadra cautella*, the genus *Heliothis*, the genus *Helicoverpa*, the genus *Agrotis, Tinea translucens, Ostrinia furnacalis, Pieris brassicae, Heliothis virescens, Plutella xylostella*, cutworm (a kind of Noctuidae) and the like;

Hemiptera pests, for example, Aphidae such as *Lipaphis erysimi, Rhopalosiphum padi, Myzus persicaem, Aphis gossypii, Aphis favae*; Aleyrodidae such as *Trialeurodes vaporariorum, Bemisia tabaci, Bemisia argentifolii; Pyrrhocoroidea, Riptortus clavatus, Nezara antennata, Unaspis yanonensis, Pseudococcus longispinis, Psylla pyricola, Stephanitis nashi, Nilaparvata lugens, Laodelphax straitellus, Sogatella furcifera, Nephotettix cincticeps* and the like;

Coleoptera pests, for example, *Phyllotreta striolata, Aulacophora femoralis, Leptinotarsa decemlineata, Phaedon cochleariae, Lissorhoptrus oryzophilus, Sitophilus zeamais, Callosobruchus chinensis, Popillia japonica, Anomala rufocuprea*, corn rootwarm, the genus *Diabrotic, Lasioderma serricorne, Lyctus brunneus, Monochamus alternatus, Anoplophora malasiaca*, the genus *Agriote, Epilachna vigintioctopunctata, Trogossitidae, Anthonomus grandis* and the like;

Orthoptera pests, for example, locust, *Locusta migratoria* and the like;

Thysanoptera pests, for example, *Thrips palmi, Scirtothrips dorsalis, Thrips tabaci, Frankliniella intonsa* and the like;

Diptera pests, for example, *Dacus cucurbitae, Bactrocera dorsalis, Agromyza oryzae* and the like;

Mites, for example, Tetranychidae such as *Tetranychus urticae, Tetranychus cinnabarinus, Tetranychus kanzawa, Panonychus citri, Panonychus ulmi*, Tenuipalpidae; *Aculops pelekassi, Aculus schlechtendali, Polyphagotarsonemus latus, Rhizoglyphus robini* and the like.

Among these, agricultural pests for which application are particularly preferred include Aphidoidea, Aleyrodoidea, Thripidae, and Tetranychidae.

There is no particular limitation for weeds which may cause stress, and examples of the weeds include gramineous weeds such as *Echinochloa crus-galli, Sorghum bicolor, Setaria faberi, Setaria viridis, Setaria glauca, Alopecurus aequalis, Digitaria ciliaris, Eleusine indica, Poa annua*; Compositae weeds such as *Xanthium strumarium, Ambrosia artemisiifolia, Ambrosia trifida, Erigeron annuus, Erigeron philadelphicus, Erigeron canadensis, Conyza sumatrensis, Youngia japonica, Conyza bonariensis, Gnaphalium japonicum, Bidens, Artemisia princeps; Oxalis corniculata, Plantago asiatica, Polygonaceae, Capsella bursa-pastoris, Cardamine flexuosa, Galium aparine, Abutilon theophrasti, Hydrocotyle sibthorpioides, Solanum nigrum, Ipomoea hederacea, Amaranthus lividus, Amaranthus viridis, Amaranthus retroflexus, Chenopodium album* var. *centrorubrum, Chenopodium album, Viola verecunda, Sida spinosa, Trifolium repens, Senna obtusifolia, Scirpus hotarui, Eleocharis acicularis, Cyperus serotinus Rottb, Monochoria vaginalis, Lindernia procumbens, Elatine triandra, Sagittaria pygmaea* and the like. Preferably, they include plant parasites such as the genus *Striga* of Scrophulariaceae and the genus *Orobanche* of Orobanchaceae, which are parasitic on cereal crops, legumes, eggplant, tomato and the like in Africa, causing significant decrease in crop yields. Further, they include *Amaranthus palmeri* of Amaranthaceae, *Ambrosia artemisiifolia* and *Erigeron canadensis* of Asteraceae, which are glyphosate resistant weeds.

There is no particular limitation for high temperature and low temperature which may cause stress. They include, for example, high temperature injury and low temperature injury which may decrease the growth and quality of rice plant, high temperature injury which may decrease the fruit setting percentage of Solanaceae crops such as tomato, high temperature injury which tends to occur particularly in tunnel cultivation and greenhouse cultivation of lettuce and the like, high temperature injury which may inhibit the growth of turves, freezing and frost damage to tea plant and fruit trees such as citrus and the like.

There is no particular limitation for excessive humidity and dryness which may cause stress. For example, they are the poor growth of crops due to excessive humidity resulting from excessive rain fall, irrigation and poorly drained soil; or the decrease in disease resistance; or the wilt of crops due to dryness resulting from the shortage of rain fall and irrigation and sandy soil and the like.

There is no particular limitation for physical properties of soil which may cause stress. For example, they are growth disorders of crops in salty soil, acidic soil or alkaline soil and the like. Among these, effects on the poor growth in salty soil and acidic soil, in particular, effects on the poor growth of crops which are weak to acidic soil such as spinach, garden pea, fava bean, onion, asparagus, lettuce, burdock are significant, and it is effective for improving the yields and qualities of these crops.

There is no particular limitation for chemical substances which may cause stress, including at least one compound selected from agricultural chemicals such as herbicides, growth regulators, plant hormones, disease resistance inducers, fungicides, insecticides, miticides; fertilizers; surfactants; allelopathy substances produced by other plants which affects crops and the like.

There is no particular limitation for agricultural chemicals which may cause stress, and examples of the chemicals include those described as substances which may affect a physiological function of a plant.

Phytotoxicity which may cause stress is, for example, phytotoxicity when treated at a concentration above the usage standard and when applied to non-intended crops, and in addition, phytotoxicity occurring under high temperature and strong light conditions and the like. Further, the application range of agricultural chemicals can be extended wider than the conventional application range because the present invention controls those phytotoxicities.

There is no particular limitation for heavy metals which may cause stress, and examples of the heavy metals include iron, zinc, copper, manganese, nickel, cobalt, tin, chromium, lead, cadmium, mercury, arsenic and the like.

Application of the chemicals composition according to the present invention to a plant can confer the resistance to stress on the plant and further can reduce phytotoxicity of the plant due to agricultural chemicals. Agricultural chemicals targeted for reducing phytotoxicity preferably include those comprising at least one selected from the group consisting fungicides, insecticides, plant growth regulators and herbicides. Further, agricultural chemicals targeted for reducing phytotoxicity preferably include those comprising the aforementioned substance (B) which affects a physiological function of a plant.

EXAMPLES

The present invention will be described in detail with reference to Examples, but the scope of the present invention shall not be limited by these.

Various substances (A) were synthesized by esterifying, glycosylating or oxidizing ascorbic acid, isoascorbic acid or dehydroascorbic acid by a known reaction. Some of the substances (A) synthesized are shown in Tables 1 and 2. $R^1$ to $R^4$ in Table 1 correspond to $R^1$ to $R^4$ in Formula (I). $R^5$ and $R^6$ in Table 2 correspond to $R^5$ and $R^6$ in Formula (II).

TABLE 1

| Compond # | $R^1$ | $R^2$ | $R^3$ | $R^4$ |
|---|---|---|---|---|
| 1 | H | H | H | H |
| 2 | $SO_3H$ | H | H | H |
| 3 | $PO_3H_2$ | H | H | H |
| 4 | glucosyl | H | H | H |
| 5 | mannosyl | H | H | H |
| 6 | galactosyl | H | H | H |
| 7 | $COCH_3$ | H | H | H |
| 8 | $COC_3H_7$-i | H | H | H |
| 9 | $COC_{17}H_{35}$-n | H | H | H |
| 10 | $COC_{16}H_{33}$-n | H | H | H |
| 11 | $COC_{18}H_{37}$-n | H | H | H |
| 12 | $CO(CH_2)_7CH\!=\!CHC_6H_{13}$-n | H | H | H |
| 13 | $COCH\!=\!CH_2$ | H | H | H |
| 14 | $COCH_2CH\!=\!CH_2$ | H | H | H |
| 15 | H | $SO_3H$ | H | H |
| 16 | H | $PO_3H_2$ | H | H |
| 17 | H | glucosyl | H | H |
| 18 | H | mannosyl | H | H |
| 19 | H | galactosyl | H | H |
| 20 | H | $COCH_3$ | H | H |
| 21 | H | $COC_3H_7$-i | H | H |
| 22 | H | $COC_{17}H_{35}$-n | H | H |
| 23 | H | $COC_{16}H_{33}$-n | H | H |
| 24 | H | $COC_{18}H_{37}$-n | H | H |
| 25 | H | $CO(CH_2)_7CH\!=\!CHC_6H_{13}$-n | H | H |
| 26 | H | $COCH\!=\!CH_2$ | H | H |
| 27 | H | $COCH_2CH\!=\!CH_2$ | H | H |
| 28 | H | H | $SO_3H$ | H |
| 29 | H | H | $PO_3H_2$ | H |
| 30 | H | H | glucosyl | H |
| 31 | H | H | mannosyl | H |
| 32 | H | H | galactosyl | H |
| 33 | H | H | $COCH_3$ | H |
| 34 | H | H | $COC_3H_7$-i | H |
| 35 | H | H | $COC_{17}H_{35}$-n | H |
| 36 | H | H | $COC_{16}H_{33}$-n | H |
| 37 | H | H | $COC_{18}H_{37}$-n | H |
| 38 | H | H | $CO(CH_2)_7CH\!=\!CHC_6H_{13}$-n | H |
| 39 | H | H | $COCH\!=\!CH_2$ | H |
| 40 | H | H | $COCH_2CH\!=\!CH_2$ | H |
| 41 | H | H | H | $SO_3H$ |
| 42 | H | H | H | $PO_3H_2$ |
| 43 | H | H | H | glucosyl |
| 44 | H | H | H | mannosyl |
| 45 | H | H | H | galactosyl |
| 46 | H | H | H | $COCH_3$ |
| 47 | H | H | H | $COC_3H_7$-i |
| 48 | H | H | H | $COC_{17}H_{35}$-n |
| 49 | H | H | H | $COC_{16}H_{33}$-n |
| 50 | H | H | H | $COC_{18}H_{37}$-n |
| 51 | H | H | H | $CO(CH_2)_7CH\!=\!CHC_6H_{13}$-n |
| 52 | H | H | H | $COCH\!=\!CH_2$ |
| 53 | H | H | H | $COCH_2CH\!=\!CH_2$ |
| 54 | $SO_3H$ | $SO_3H$ | H | H |
| 55 | $SO_3H$ | $PO_3H_2$ | H | H |
| 56 | $SO_3H$ | glucosyl | H | H |
| 57 | $SO_3H$ | mannosyl | H | H |
| 58 | $SO_3H$ | galactosyl | H | H |
| 59 | $SO_3H$ | $COCH_3$ | H | H |

TABLE 1-continued

| Compond # | R$^1$ | R$^2$ | R$^3$ | R$^4$ |
|---|---|---|---|---|
| 60 | SO$_3$H | COC$_3$H$_7$-i | H | H |
| 61 | SO$_3$H | COC$_{17}$H$_{35}$-n | H | H |
| 62 | SO$_3$H | COC$_{16}$H$_{33}$-n | H | H |
| 63 | SO$_3$H | COC$_{18}$H$_{37}$-n | H | H |
| 64 | SO$_3$H | CO(CH$_2$)$_7$CH=CHC$_6$H$_{13}$-n | H | H |
| 65 | SO$_3$H | COCH=CH$_2$ | H | H |
| 66 | SO$_3$H | COCH$_2$CH=CH$_2$ | H | H |
| 67 | SO$_3$H | SO$_3$H | H | H |
| 68 | SO$_3$H | PO$_3$H$_2$ | H | H |
| 69 | SO$_3$H | glucosyl | H | H |
| 70 | SO$_3$H | mannosyl | H | H |
| 71 | SO$_3$H | galactosyl | H | H |
| 72 | SO$_3$H | COCH$_3$ | H | H |
| 73 | SO$_3$H | COC$_3$H$_7$-i | H | H |
| 74 | SO$_3$H | COC$_{17}$H$_{35}$-n | H | H |
| 75 | SO$_3$H | COC$_{16}$H$_{33}$-n | H | H |
| 76 | SO$_3$H | COC$_{18}$H$_{37}$-n | H | H |
| 77 | SO$_3$H | CO(CH$_2$)$_7$CH=CHC$_6$H$_{13}$-n | H | H |
| 78 | SO$_3$H | COCH=CH$_2$ | H | H |
| 79 | SO$_3$H | COCH$_2$CH=CH$_2$ | H | H |
| 80 | glucosyl | SO$_3$H | H | H |
| 81 | glucosyl | PO$_3$H$_2$ | H | H |
| 82 | glucosyl | glucosyl | H | H |
| 83 | glucosyl | mannosyl | H | H |
| 84 | glucosyl | galactosyl | H | H |
| 85 | glucosyl | COCH$_3$ | H | H |
| 86 | glucosyl | COC$_3$H$_7$-i | H | H |
| 87 | glucosyl | COC$_{17}$H$_{35}$-n | H | H |
| 88 | glucosyl | COC$_{16}$H$_{33}$-n | H | H |
| 89 | glucosyl | COC$_{18}$H$_{37}$-n | H | H |
| 90 | glucosyl | CO(CH$_2$)$_7$CH=CHC$_6$H$_{13}$-n | H | H |
| 91 | glucosyl | COCH=CH$_2$ | H | H |
| 92 | glucosyl | COCH$_2$CH=CH$_2$ | H | H |
| 93 | COC$_{16}$H$_{33}$ | SO$_3$H | H | H |
| 94 | COC$_{16}$H$_{33}$ | PO$_3$H$_2$ | H | H |
| 95 | COC$_{16}$H$_{33}$ | glucosyl | H | H |
| 96 | COC$_{16}$H$_{33}$ | mannosyl | H | H |
| 97 | COC$_{16}$H$_{33}$ | galactosyl | H | H |
| 98 | COC$_{16}$H$_{33}$ | COCH$_3$ | H | H |
| 99 | COC$_{16}$H$_{33}$ | COC$_3$H$_7$-i | H | H |
| 100 | COC$_{16}$H$_{33}$ | COC$_{17}$H$_{35}$-n | H | H |
| 101 | COC$_{16}$H$_{33}$ | COC$_{16}$H$_{33}$-n | H | H |
| 102 | COC$_{16}$H$_{33}$ | COC$_{18}$H$_{37}$-n | H | H |
| 103 | COC$_{16}$H$_{33}$ | CO(CH$_2$)$_7$CH=CHC$_6$H$_{13}$-n | H | H |
| 104 | COC$_{16}$H$_{33}$ | COCH=CH$_2$ | H | H |
| 105 | COC$_{16}$H$_{33}$ | COCH$_2$CH=CH$_2$ | H | H |
| 106 | CO(CH$_2$)$_7$CH=CHC$_6$H$_{13}$ | SO$_3$H | H | H |
| 107 | CO(CH$_2$)$_7$CH=CHC$_6$H$_{13}$ | PO$_3$H$_2$ | H | H |
| 108 | CO(CH$_2$)$_7$CH=CHC$_6$H$_{13}$ | glucosyl | H | H |
| 109 | CO(CH$_2$)$_7$CH=CHC$_6$H$_{13}$ | mannosyl | H | H |
| 110 | CO(CH$_2$)$_7$CH=CHC$_6$H$_{13}$ | galactosyl | H | H |
| 111 | CO(CH$_2$)$_7$CH=CHC$_6$H$_{13}$ | COCH$_3$ | H | H |
| 112 | CO(CH$_2$)$_7$CH=CHC$_6$H$_{13}$ | COC$_3$H$_7$-i | H | H |
| 113 | CO(CH$_2$)$_7$CH=CHC$_6$H$_{13}$ | COC$_{17}$H$_{35}$-n | H | H |
| 114 | CO(CH$_2$)$_7$CH=CHC$_6$H$_{13}$ | COC$_{16}$H$_{33}$-n | H | H |
| 115 | CO(CH$_2$)$_7$CH=CHC$_6$H$_{13}$ | COC$_{18}$H$_{37}$-n | H | H |
| 116 | CO(CH$_2$)$_7$CH=CHC$_6$H$_{13}$ | CO(CH$_2$)$_7$CH=CHC$_6$H$_{13}$-n | H | H |
| 117 | CO(CH$_2$)$_7$CH=CHC$_6$H$_{13}$ | COCH=CH$_2$ | H | H |
| 118 | CO(CH$_2$)$_7$CH=CHC$_6$H$_{13}$ | COCH$_2$CH=CH$_2$ | H | H |
| 119 | SO$_3$H | H | SO$_3$H | H |
| 120 | SO$_3$H | H | PO$_3$H$_2$ | H |
| 121 | SO$_3$H | H | glucosyl | H |
| 122 | SO$_3$H | H | mannosyl | H |
| 123 | SO$_3$H | H | galactosyl | H |
| 124 | SO$_3$H | H | COCH$_3$ | H |
| 125 | SO$_3$H | H | COC$_3$H$_7$-i | H |
| 126 | SO$_3$H | H | COC$_{17}$H$_{35}$-n | H |
| 127 | SO$_3$H | H | COC$_{16}$H$_{33}$-n | H |
| 128 | SO$_3$H | H | COC$_{18}$H$_{37}$-n | H |
| 129 | SO$_3$H | H | CO(CH$_2$)$_7$CH=CHC$_6$H$_{13}$-n | H |
| 130 | SO$_3$H | H | COCH=CH$_2$ | H |
| 131 | SO$_3$H | H | COCH$_2$CH=CH$_2$ | H |
| 132 | PO$_3$H$_2$ | H | SO$_3$H | H |
| 133 | PO$_3$H$_2$ | H | PO$_3$H$_2$ | H |
| 134 | PO$_3$H$_2$ | H | glucosyl | H |
| 135 | PO$_3$H$_2$ | H | mannosyl | H |
| 136 | PO$_3$H$_2$ | H | galactosyl | H |
| 137 | PO$_3$H$_2$ | H | COCH$_3$ | H |

TABLE 1-continued

| Compond # | R$^1$ | R$^2$ | R$^3$ | R$^4$ |
|---|---|---|---|---|
| 138 | PO$_3$H$_2$ | H | COC$_3$H$_7$-i | H |
| 139 | PO$_3$H$_2$ | H | COC$_{17}$H$_{35}$-n | H |
| 140 | PO$_3$H$_2$ | H | COC$_{16}$H$_{33}$-n | H |
| 141 | PO$_3$H$_2$ | H | COC$_{18}$H$_{37}$-n | H |
| 142 | PO$_3$H$_2$ | H | CO(CH$_2$)$_7$CH=CHC$_6$H$_{13}$-n | H |
| 143 | PO$_3$H$_2$ | H | COCH=CH$_2$ | H |
| 144 | PO$_3$H$_2$ | H | COCH$_2$CH=CH$_2$ | H |
| 145 | glucosyl | H | SO$_3$H | H |
| 146 | glucosyl | H | PO$_3$H$_2$ | H |
| 147 | glucosyl | H | glucosyl | H |
| 148 | glucosyl | H | mannosyl | H |
| 149 | glucosyl | H | galactosyl | H |
| 150 | glucosyl | H | COCH$_3$ | H |
| 151 | glucosyl | H | COC$_3$H$_7$-i | H |
| 152 | glucosyl | H | COC$_{17}$H$_{35}$-n | H |
| 153 | glucosyl | H | COC$_{16}$H$_{33}$-n | H |
| 154 | glucosyl | H | COC$_{18}$H$_{37}$-n | H |
| 155 | glucosyl | H | CO(CH$_2$)$_7$CH=CHC$_6$H$_{13}$-n | H |
| 156 | glucosyl | H | COCH=CH$_2$ | H |
| 157 | glucosyl | H | COCH$_2$CH=CH$_2$ | H |
| 158 | COC$_{16}$H$_{33}$-n | H | SO$_3$H | H |
| 159 | COC$_{16}$H$_{33}$-n | H | PO$_3$H$_2$ | H |
| 160 | COC$_{16}$H$_{33}$-n | H | glucosyl | H |
| 161 | COC$_{16}$H$_{33}$-n | H | mannosyl | H |
| 162 | COC$_{16}$H$_{33}$-n | H | galactosyl | H |
| 163 | COC$_{16}$H$_{33}$-n | H | COCH$_3$ | H |
| 164 | COC$_{16}$H$_{33}$-n | H | COC$_3$H$_7$-i | H |
| 165 | COC$_{16}$H$_{33}$-n | H | COC$_{17}$H$_{35}$-n | H |
| 166 | COC$_{16}$H$_{33}$-n | H | COC$_{16}$H$_{33}$-n | H |
| 167 | COC$_{16}$H$_{33}$-n | H | COC$_{18}$H$_{37}$-n | H |
| 168 | COC$_{16}$H$_{33}$-n | H | CO(CH$_2$)$_7$CH=CHC$_6$H$_{13}$-n | H |
| 169 | COC$_{16}$H$_{33}$-n | H | COCH=CH$_2$ | H |
| 170 | COC$_{16}$H$_{33}$-n | H | COCH$_2$CH=CH$_2$ | H |
| 171 | CO(CH$_2$)$_7$CH=CHC$_6$H$_{13}$-n | H | SO$_3$H | H |
| 172 | CO(CH$_2$)$_7$CH=CHC$_6$H$_{13}$-n | H | PO$_3$H$_2$ | H |
| 173 | CO(CH$_2$)$_7$CH=CHC$_6$H$_{13}$-n | H | glucosyl | H |
| 174 | CO(CH$_2$)$_7$CH=CHC$_6$H$_{13}$-n | H | mannosyl | H |
| 175 | CO(CH$_2$)$_7$CH=CHC$_6$H$_{13}$-n | H | galactosyl | H |
| 176 | CO(CH$_2$)$_7$CH=CHC$_6$H$_{13}$-n | H | COCH$_3$ | H |
| 177 | CO(CH$_2$)$_7$CH=CHC$_6$H$_{13}$-n | H | COC$_3$H$_7$-i | H |
| 178 | CO(CH$_2$)$_7$CH=CHC$_6$H$_{13}$-n | H | COC$_{17}$H$_{35}$-n | H |
| 179 | CO(CH$_2$)$_7$CH=CHC$_6$H$_{13}$-n | H | COC$_{16}$H$_{33}$-n | H |
| 180 | CO(CH$_2$)$_7$CH=CHC$_6$H$_{13}$-n | H | COC$_{18}$H$_{37}$-n | H |
| 181 | CO(CH$_2$)$_7$CH=CHC$_6$H$_{13}$-n | H | CO(CH$_2$)$_7$CH=CHC$_6$H$_{13}$-n | H |
| 182 | CO(CH$_2$)$_7$CH=CHC$_6$H$_{13}$-n | H | COCH=CH$_2$ | H |
| 183 | CO(CH$_2$)$_7$CH=CHC$_6$H$_{13}$-n | H | COCH$_2$CH=CH$_2$ | H |
| 184 | SO$_3$H | H | H | SO$_3$H |
| 185 | SO$_3$H | H | H | PO$_3$H$_2$ |
| 186 | SO$_3$H | H | H | glucosyl |
| 187 | SO$_3$H | H | H | mannosyl |
| 188 | SO$_3$H | H | H | galactosyl |
| 189 | SO$_3$H | H | H | COCH$_3$ |
| 190 | SO$_3$H | H | H | COC$_3$H$_7$-i |
| 191 | SO$_3$H | H | H | COC$_{17}$H$_{35}$-n |
| 192 | SO$_3$H | H | H | COC$_{16}$H$_{33}$-n |
| 193 | SO$_3$H | H | H | COC$_{18}$H$_{37}$-n |
| 194 | SO$_3$H | H | H | CO(CH$_2$)$_7$CH=CHC$_6$H$_{13}$-n |
| 195 | SO$_3$H | H | H | COCH=CH$_2$ |
| 196 | SO$_3$H | H | H | COCH$_2$CH=CH$_2$ |
| 197 | PO$_3$H$_2$ | H | H | SO$_3$H |
| 198 | PO$_3$H$_2$ | H | H | PO$_3$H$_2$ |
| 199 | PO$_3$H$_2$ | H | H | glucosyl |
| 200 | PO$_3$H$_2$ | H | H | mannosyl |
| 201 | PO$_3$H$_2$ | H | H | galactosyl |
| 202 | PO$_3$H$_2$ | H | H | COCH$_3$ |
| 203 | PO$_3$H$_2$ | H | H | COC$_3$H$_7$-i |
| 204 | PO$_3$H$_2$ | H | H | COC$_{17}$H$_{35}$-n |
| 205 | PO$_3$H$_2$ | H | H | COC$_{16}$H$_{33}$-n |
| 206 | PO$_3$H$_2$ | H | H | COC$_{18}$H$_{37}$-n |
| 207 | PO$_3$H$_2$ | H | H | CO(CH$_2$)$_7$CH=CHC$_6$H$_{13}$-n |
| 208 | PO$_3$H$_2$ | H | H | COCH=CH$_2$ |
| 209 | PO$_3$H$_2$ | H | H | COCH$_2$CH=CH$_2$ |
| 210 | glucosyl | H | H | SO$_3$H |
| 211 | glucosyl | H | H | PO$_3$H$_2$ |
| 212 | glucosyl | H | H | glucosyl |
| 213 | glucosyl | H | H | mannosyl |
| 214 | glucosyl | H | H | galactosyl |
| 215 | glucosyl | H | H | COCH$_3$ |

TABLE 1-continued

| Compond # | R$^1$ | R$^2$ | R$^3$ | R$^4$ |
|---|---|---|---|---|
| 216 | glucosyl | H | H | COC$_3$H$_7$-i |
| 217 | glucosyl | H | H | COC$_{17}$H$_{35}$-n |
| 218 | glucosyl | H | H | COC$_{16}$H$_{33}$-n |
| 219 | glucosyl | H | H | COC$_{18}$H$_{37}$-n |
| 220 | glucosyl | H | H | CO(CH$_2$)$_7$CH=CHC$_6$H$_{13}$-n |
| 221 | glucosyl | H | H | COCH=CH$_2$ |
| 222 | glucosyl | H | H | COCH$_2$CH=CH$_2$ |
| 223 | COC$_{16}$H$_{33}$-n | H | H | SO$_3$H |
| 224 | COC$_{16}$H$_{33}$-n | H | H | PO$_3$H$_2$ |
| 225 | COC$_{16}$H$_{33}$-n | H | H | glucosyl |
| 226 | COC$_{16}$H$_{33}$-n | H | H | mannosyl |
| 227 | COC$_{16}$H$_{33}$-n | H | H | galactosyl |
| 228 | COC$_{16}$H$_{33}$-n | H | H | COCH$_3$ |
| 229 | COC$_{16}$H$_{33}$-n | H | H | COC$_3$H$_7$-i |
| 230 | COC$_{16}$H$_{33}$-n | H | H | COC$_{17}$H$_{35}$-n |
| 231 | COC$_{16}$H$_{33}$-n | H | H | COC$_{16}$H$_{33}$-n |
| 232 | COC$_{16}$H$_{33}$-n | H | H | COC$_{18}$H$_{37}$-n |
| 233 | COC$_{16}$H$_{33}$-n | H | H | CO(CH$_2$)$_7$CH=CHC$_6$H$_{13}$-n |
| 234 | COC$_{16}$H$_{33}$-n | H | H | COCH=CH$_2$ |
| 235 | COC$_{16}$H$_{33}$-n | H | H | COCH$_2$CH=CH$_2$ |
| 236 | CO(CH$_2$)$_7$CH=CHC$_6$H$_{13}$-n | H | H | SO$_3$H |
| 237 | CO(CH$_2$)$_7$CH=CHC$_6$H$_{13}$-n | H | H | PO$_3$H$_2$ |
| 238 | CO(CH$_2$)$_7$CH=CHC$_6$H$_{13}$-n | H | H | glucosyl |
| 239 | CO(CH$_2$)$_7$CH=CHC$_6$H$_{13}$-n | H | H | mannosyl |
| 240 | CO(CH$_2$)$_7$CH=CHC$_6$H$_{13}$-n | H | H | galactosyl |
| 241 | CO(CH$_2$)$_7$CH=CHC$_6$H$_{13}$-n | H | H | COCH$_3$ |
| 242 | CO(CH$_2$)$_7$CH=CHC$_6$H$_{13}$-n | H | H | COC$_3$H$_7$-i |
| 243 | CO(CH$_2$)$_7$CH=CHC$_6$H$_{13}$-n | H | H | COC$_{17}$H$_{35}$-n |
| 244 | CO(CH$_2$)$_7$CH=CHC$_6$H$_{13}$-n | H | H | COC$_{16}$H$_{33}$-n |
| 245 | CO(CH$_2$)$_7$CH=CHC$_6$H$_{13}$-n | H | H | COC$_{18}$H$_{37}$-n |
| 246 | CO(CH$_2$)$_7$CH=CHC$_6$H$_{13}$-n | H | H | CO(CH$_2$)$_7$CH=CHC$_6$H$_{13}$-n |
| 247 | CO(CH$_2$)$_7$CH=CHC$_6$H$_{13}$-n | H | H | COCH=CH$_2$ |
| 248 | CO(CH$_2$)$_7$CH=CHC$_6$H$_{13}$-n | H | H | COCH$_2$CH=CH$_2$ |
| 249 | SO$_3$H | SO$_3$H | SO$_3$H | H |
| 250 | SO$_3$H | SO$_3$H | PO$_3$H$_2$ | H |
| 251 | SO$_3$H | SO$_3$H | glucosyl | H |
| 252 | SO$_3$H | SO$_3$H | mannosyl | H |
| 253 | SO$_3$H | SO$_3$H | galactosyl | H |
| 254 | SO$_3$H | SO$_3$H | COCH$_3$ | H |
| 255 | SO$_3$H | SO$_3$H | COC$_3$H$_7$-i | H |
| 256 | SO$_3$H | SO$_3$H | COC$_{17}$H$_{35}$-n | H |
| 257 | SO$_3$H | SO$_3$H | COC$_{16}$H$_{33}$-n | H |
| 258 | SO$_3$H | SO$_3$H | COC$_{18}$H$_{37}$-n | H |
| 259 | SO$_3$H | SO$_3$H | CO(CH$_2$)$_7$CH=CHC$_6$H$_{13}$-n | H |
| 260 | SO$_3$H | SO$_3$H | COCH=CH$_2$ | H |
| 261 | SO$_3$H | SO$_3$H | COCH$_2$CH=CH$_2$ | H |
| 262 | PO$_3$H$_2$ | PO$_3$H$_2$ | SO$_3$H | H |
| 263 | PO$_3$H$_2$ | PO$_3$H$_2$ | PO$_3$H$_2$ | H |
| 264 | PO$_3$H$_2$ | PO$_3$H$_2$ | glucosyl | H |
| 265 | PO$_3$H$_2$ | PO$_3$H$_2$ | mannosyl | H |
| 266 | PO$_3$H$_2$ | PO$_3$H$_2$ | galactosyl | H |
| 267 | PO$_3$H$_2$ | PO$_3$H$_2$ | COCH$_3$ | H |
| 268 | PO$_3$H$_2$ | PO$_3$H$_2$ | COC$_3$H$_7$-i | H |
| 269 | PO$_3$H$_2$ | PO$_3$H$_2$ | COC$_{17}$H$_{35}$-n | H |
| 270 | PO$_3$H$_2$ | PO$_3$H$_2$ | COC$_{16}$H$_{33}$-n | H |
| 271 | PO$_3$H$_2$ | PO$_3$H$_2$ | COC$_{18}$H$_{37}$-n | H |
| 272 | PO$_3$H$_2$ | PO$_3$H$_2$ | CO(CH$_2$)$_7$CH=CHC$_6$H$_{13}$-n | H |
| 273 | PO$_3$H$_2$ | PO$_3$H$_2$ | COCH=CH$_2$ | H |
| 274 | PO$_3$H$_2$ | PO$_3$H$_2$ | COCH$_2$CH=CH$_2$ | H |
| 275 | glucosyl | glucosyl | SO$_3$H | H |
| 276 | glucosyl | glucosyl | PO$_3$H$_2$ | H |
| 277 | glucosyl | glucosyl | glucosyl | H |
| 278 | glucosyl | glucosyl | mannosyl | H |
| 279 | glucosyl | glucosyl | galactosyl | H |
| 280 | glucosyl | glucosyl | COCH$_3$ | H |
| 281 | glucosyl | glucosyl | COC$_3$H$_7$-i | H |
| 282 | glucosyl | glucosyl | COC$_{17}$H$_{35}$-n | H |
| 283 | glucosyl | glucosyl | COC$_{16}$H$_{33}$-n | H |
| 284 | glucosyl | glucosyl | COC$_{18}$H$_{37}$-n | H |
| 285 | glucosyl | glucosyl | CO(CH$_2$)$_7$CH=CHC$_6$H$_{13}$-n | H |
| 286 | glucosyl | glucosyl | COCH=CH$_2$ | H |
| 287 | glucosyl | glucosyl | COCH$_2$CH=CH$_2$ | H |
| 288 | COC$_{16}$H$_{33}$-n | COC$_{16}$H$_{33}$-n | SO$_3$H | H |
| 289 | COC$_{16}$H$_{33}$-n | COC$_{16}$H$_{33}$-n | PO$_3$H$_2$ | H |
| 290 | COC$_{16}$H$_{33}$-n | COC$_{16}$H$_{33}$-n | glucosyl | H |
| 291 | COC$_{16}$H$_{33}$-n | COC$_{16}$H$_{33}$-n | mannosyl | H |
| 292 | COC$_{16}$H$_{33}$-n | COC$_{16}$H$_{33}$-n | galactosyl | H |
| 293 | COC$_{16}$H$_{33}$-n | COC$_{16}$H$_{33}$-n | COCH$_3$ | H |

TABLE 1-continued

| Compond # | $R^1$ | $R^2$ | $R^3$ | $R^4$ |
|---|---|---|---|---|
| 294 | $COC_{16}H_{33}$-n | $COC_{16}H_{33}$-n | $COC_3H_7$-i | H |
| 295 | $COC_{16}H_{33}$-n | $COC_{16}H_{33}$-n | $COC_{17}H_{35}$-n | H |
| 296 | $COC_{16}H_{33}$-n | $COC_{16}H_{33}$-n | $COC_{16}H_{33}$-n | H |
| 297 | $COC_{16}H_{33}$-n | $COC_{16}H_{33}$-n | $COC_{18}H_{37}$-n | H |
| 298 | $COC_{16}H_{33}$-n | $COC_{16}H_{33}$-n | $CO(CH_2)_7CH=CHC_6H_{13}$-n | H |
| 299 | $COC_{16}H_{33}$-n | $COC_{16}H_{33}$-n | $COCH=CH_2$ | H |
| 300 | $COC_{16}H_{33}$-n | $COC_{16}H_{33}$-n | $COCH_2CH=CH_2$ | H |
| 301 | $CO(CH_2)_7CH=CHC_6H_{13}$-n | $CO(CH_2)_7CH=CHC_6H_{13}$-n | $SO_3H$ | H |
| 302 | $CO(CH_2)_7CH=CHC_6H_{13}$-n | $CO(CH_2)_7CH=CHC_6H_{13}$-n | $PO_3H_2$ | H |
| 303 | $CO(CH_2)_7CH=CHC_6H_{13}$-n | $CO(CH_2)_7CH=CHC_6H_{13}$-n | glucosyl | H |
| 304 | $CO(CH_2)_7CH=CHC_6H_{13}$-n | $CO(CH_2)_7CH=CHC_6H_{13}$-n | mannosyl | H |
| 305 | $CO(CH_2)_7CH=CHC_6H_{13}$-n | $CO(CH_2)_7CH=CHC_6H_{13}$-n | galactosyl | H |
| 306 | $CO(CH_2)_7CH=CHC_6H_{13}$-n | $CO(CH_2)_7CH=CHC_6H_{13}$-n | $COCH_3$ | H |
| 307 | $CO(CH_2)_7CH=CHC_6H_{13}$-n | $CO(CH_2)_7CH=CHC_6H_{13}$-n | $COC_3H_7$-i | H |
| 308 | $CO(CH_2)_7CH=CHC_6H_{13}$-n | $CO(CH_2)_7CH=CHC_6H_{13}$-n | $COC_{17}H_{35}$-n | H |
| 309 | $CO(CH_2)_7CH=CHC_6H_{13}$-n | $CO(CH_2)_7CH=CHC_6H_{13}$-n | $COC_{16}H_{33}$-n | H |
| 310 | $CO(CH_2)_7CH=CHC_6H_{13}$-n | $CO(CH_2)_7CH=CHC_6H_{13}$-n | $COC_{18}H_{37}$-n | H |
| 311 | $CO(CH_2)_7CH=CHC_6H_{13}$-n | $CO(CH_2)_7CH=CHC_6H_{13}$-n | $CO(CH_2)_7CH=CHC_6H_{13}$-n | H |
| 312 | $CO(CH_2)_7CH=CHC_6H_{13}$-n | $CO(CH_2)_7CH=CHC_6H_{13}$-n | $COCH=CH_2$ | H |
| 313 | $CO(CH_2)_7CH=CHC_6H_{13}$-n | $CO(CH_2)_7CH=CHC_6H_{13}$-n | $COCH_2CH=CH_2$ | H |
| 314 | $SO_3H$ | $SO_3H$ | H | $SO_3H$ |
| 315 | $SO_3H$ | $SO_3H$ | H | $PO_3H_2$ |
| 316 | $SO_3H$ | $SO_3H$ | H | glucosyl |
| 317 | $SO_3H$ | $SO_3H$ | H | mannosyl |
| 318 | $SO_3H$ | $SO_3H$ | H | galactosyl |
| 319 | $SO_3H$ | $SO_3H$ | H | $COCH_3$ |
| 320 | $SO_3H$ | $SO_3H$ | H | $COC_3H_7$-i |
| 321 | $SO_3H$ | $SO_3H$ | H | $COC_{17}H_{35}$-n |
| 322 | $SO_3H$ | $SO_3H$ | H | $COC_{16}H_{33}$-n |
| 323 | $SO_3H$ | $SO_3H$ | H | $COC_{18}H_{37}$-n |
| 324 | $SO_3H$ | $SO_3H$ | H | $CO(CH_2)_7CH=CHC_6H_{13}$-n |
| 325 | $SO_3H$ | $SO_3H$ | H | $COCH=CH_2$ |
| 326 | $SO_3H$ | $SO_3H$ | H | $COCH_2CH=CH_2$ |
| 327 | $PO_3H_2$ | $PO_3H_2$ | H | $SO_3H$ |
| 328 | $PO_3H_2$ | $PO_3H_2$ | H | $PO_3H_2$ |
| 329 | $PO_3H_2$ | $PO_3H_2$ | H | glucosyl |
| 330 | $PO_3H_2$ | $PO_3H_2$ | H | mannosyl |
| 331 | $PO_3H_2$ | $PO_3H_2$ | H | galactosyl |
| 332 | $PO_3H_2$ | $PO_3H_2$ | H | $COCH_3$ |
| 333 | $PO_3H_2$ | $PO_3H_2$ | H | $COC_3H_7$-i |
| 334 | $PO_3H_2$ | $PO_3H_2$ | H | $COC_{17}H_{35}$-n |
| 335 | $PO_3H_2$ | $PO_3H_2$ | H | $COC_{16}H_{33}$-n |
| 336 | $PO_3H_2$ | $PO_3H_2$ | H | $COC_{18}H_{37}$-n |
| 337 | $PO_3H_2$ | $PO_3H_2$ | H | $CO(CH_2)_7CH=CHC_6H_{13}$-n |
| 338 | $PO_3H_2$ | $PO_3H_2$ | H | $COCH=CH_2$ |
| 339 | $PO_3H_2$ | $PO_3H_2$ | H | $COCH_2CH=CH_2$ |
| 340 | glucosyl | glucosyl | H | $SO_3H$ |
| 341 | glucosyl | glucosyl | H | $PO_3H_2$ |
| 342 | glucosyl | glucosyl | H | glucosyl |
| 343 | glucosyl | glucosyl | H | mannosyl |
| 344 | glucosyl | glucosyl | H | galactosyl |
| 345 | glucosyl | glucosyl | H | $COCH_3$ |
| 346 | glucosyl | glucosyl | H | $COC_3H_7$-i |
| 347 | glucosyl | glucosyl | H | $COC_{17}H_{35}$-n |
| 348 | glucosyl | glucosyl | H | $COC_{16}H_{33}$-n |
| 349 | glucosyl | glucosyl | H | $COC_{18}H_{37}$-n |
| 350 | glucosyl | glucosyl | H | $CO(CH_2)_7CH=CHC_6H_{13}$-n |
| 351 | glucosyl | glucosyl | H | $COCH=CH_2$ |
| 352 | glucosyl | glucosyl | H | $COCH_2CH=CH_2$ |
| 353 | $COC_{16}H_{33}$-n | $COC_{16}H_{33}$-n | H | $SO_3H$ |
| 354 | $COC_{16}H_{33}$-n | $COC_{16}H_{33}$-n | H | $PO_3H_2$ |
| 355 | $COC_{16}H_{33}$-n | $COC_{16}H_{33}$-n | H | glucosyl |
| 356 | $COC_{16}H_{33}$-n | $COC_{16}H_{33}$-n | H | mannosyl |
| 357 | $COC_{16}H_{33}$-n | $COC_{16}H_{33}$-n | H | galactosyl |
| 358 | $COC_{16}H_{33}$-n | $COC_{16}H_{33}$-n | H | $COCH_3$ |
| 359 | $COC_{16}H_{33}$-n | $COC_{16}H_{33}$-n | H | $COC_3H_7$-i |
| 360 | $COC_{16}H_{33}$-n | $COC_{16}H_{33}$-n | H | $COC_{17}H_{35}$-n |
| 361 | $COC_{16}H_{33}$-n | $COC_{16}H_{33}$-n | H | $COC_{16}H_{33}$-n |
| 362 | $COC_{16}H_{33}$-n | $COC_{16}H_{33}$-n | H | $COC_{18}H_{37}$-n |
| 363 | $COC_{16}H_{33}$-n | $COC_{16}H_{33}$-n | H | $CO(CH_2)_7CH=CHC_6H_{13}$-n |
| 364 | $COC_{16}H_{33}$-n | $COC_{16}H_{33}$-n | H | $COCH=CH_2$ |
| 365 | $COC_{16}H_{33}$-n | $COC_{16}H_{33}$-n | H | $COCH_2CH=CH_2$ |
| 366 | $CO(CH_2)_7CH=CHC_6H_{13}$-n | $CO(CH_2)_7CH=CHC_6H_{13}$-n | H | $SO_3H$ |
| 367 | $CO(CH_2)_7CH=CHC_6H_{13}$-n | $CO(CH_2)_7CH=CHC_6H_{13}$-n | H | $PO_3H_2$ |
| 368 | $CO(CH_2)_7CH=CHC_6H_{13}$-n | $CO(CH_2)_7CH=CHC_6H_{13}$-n | H | glucosyl |
| 369 | $CO(CH_2)_7CH=CHC_6H_{13}$-n | $CO(CH_2)_7CH=CHC_6H_{13}$-n | H | mannosyl |
| 370 | $CO(CH_2)_7CH=CHC_6H_{13}$-n | $CO(CH_2)_7CH=CHC_6H_{13}$-n | H | galactosyl |
| 371 | $CO(CH_2)_7CH=CHC_6H_{13}$-n | $CO(CH_2)_7CH=CHC_6H_{13}$-n | H | $COCH_3$ |

TABLE 1-continued

| Compond # | R$^1$ | R$^2$ | R$^3$ | R$^4$ |
|---|---|---|---|---|
| 372 | CO(CH$_2$)$_7$CH=CHC$_6$H$_{13}$-n | CO(CH$_2$)$_7$CH=CHC$_6$H$_{13}$-n | H | COC$_3$H$_7$-i |
| 373 | CO(CH$_2$)$_7$CH=CHC$_6$H$_{13}$-n | CO(CH$_2$)$_7$CH=CHC$_6$H$_{13}$-n | H | COC$_{17}$H$_{35}$-n |
| 374 | CO(CH$_2$)$_7$CH=CHC$_6$H$_{13}$-n | CO(CH$_2$)$_7$CH=CHC$_6$H$_{13}$-n | H | COC$_{16}$H$_{33}$-n |
| 375 | CO(CH$_2$)$_7$CH=CHC$_6$H$_{13}$-n | CO(CH$_2$)$_7$CH=CHC$_6$H$_{13}$-n | H | COC$_{18}$H$_{37}$-n |
| 376 | CO(CH$_2$)$_7$CH=CHC$_6$H$_{13}$-n | CO(CH$_2$)$_7$CH=CHC$_6$H$_{13}$-n | H | CO(CH$_2$)$_7$CH=CHC$_6$H$_{13}$-n |
| 377 | CO(CH$_2$)$_7$CH=CHC$_6$H$_{13}$-n | CO(CH$_2$)$_7$CH=CHC$_6$H$_{13}$-n | H | COCH=CH$_2$ |
| 378 | CO(CH$_2$)$_7$CH=CHC$_6$H$_{13}$-n | CO(CH$_2$)$_7$CH=CHC$_6$H$_{13}$-n | H | COCH$_2$CH=CH$_2$ |
| 379 | SO$_3$H | SO$_3$H | SO$_3$H | SO$_3$H |
| 380 | SO$_3$H | SO$_3$H | SO$_3$H | PO$_3$H$_2$ |
| 381 | SO$_3$H | SO$_3$H | SO$_3$H | glucosyl |
| 382 | SO$_3$H | SO$_3$H | SO$_3$H | mannosyl |
| 383 | SO$_3$H | SO$_3$H | SO$_3$H | galactosyl |
| 384 | SO$_3$H | SO$_3$H | SO$_3$H | COCH$_3$ |
| 385 | SO$_3$H | SO$_3$H | SO$_3$H | COC$_3$H$_7$-i |
| 386 | SO$_3$H | SO$_3$H | SO$_3$H | COC$_{17}$H$_{35}$-n |
| 387 | SO$_3$H | SO$_3$H | SO$_3$H | COC$_{16}$H$_{33}$-n |
| 388 | SO$_3$H | SO$_3$H | SO$_3$H | COC$_{18}$H$_{37}$-n |
| 389 | SO$_3$H | SO$_3$H | SO$_3$H | CO(CH$_2$)$_7$CH=CHC$_6$H$_{13}$-n |
| 390 | SO$_3$H | SO$_3$H | SO$_3$H | COCH=CH$_2$ |
| 391 | SO$_3$H | SO$_3$H | SO$_3$H | COCH$_2$CH=CH$_2$ |
| 392 | PO$_3$H$_2$ | PO$_3$H$_2$ | PO$_3$H$_2$ | SO$_3$H |
| 393 | PO$_3$H$_2$ | PO$_3$H$_2$ | PO$_3$H$_2$ | PO$_3$H$_2$ |
| 394 | PO$_3$H$_2$ | PO$_3$H$_2$ | PO$_3$H$_2$ | glucosyl |
| 395 | PO$_3$H$_2$ | PO$_3$H$_2$ | PO$_3$H$_2$ | mannosyl |
| 396 | PO$_3$H$_2$ | PO$_3$H$_2$ | PO$_3$H$_2$ | galactosyl |
| 397 | PO$_3$H$_2$ | PO$_3$H$_2$ | PO$_3$H$_2$ | COCH$_3$ |
| 398 | PO$_3$H$_2$ | PO$_3$H$_2$ | PO$_3$H$_2$ | COC$_3$H$_7$-i |
| 399 | PO$_3$H$_2$ | PO$_3$H$_2$ | PO$_3$H$_2$ | COC$_{17}$H$_{35}$-n |
| 400 | PO$_3$H$_2$ | PO$_3$H$_2$ | PO$_3$H$_2$ | COC$_{16}$H$_{33}$-n |
| 401 | PO$_3$H$_2$ | PO$_3$H$_2$ | PO$_3$H$_2$ | COC$_{18}$H$_{37}$-n |
| 402 | PO$_3$H$_2$ | PO$_3$H$_2$ | PO$_3$H$_2$ | CO(CH$_2$)$_7$CH=CHC$_6$H$_{13}$-n |
| 403 | PO$_3$H$_2$ | PO$_3$H$_2$ | PO$_3$H$_2$ | COCH=CH$_2$ |
| 404 | PO$_3$H$_2$ | PO$_3$H$_2$ | PO$_3$H$_2$ | COCH$_2$CH=CH$_2$ |
| 405 | glucosyl | glucosyl | glucosyl | SO$_3$H |
| 406 | glucosyl | glucosyl | glucosyl | PO$_3$H$_2$ |
| 407 | glucosyl | glucosyl | glucosyl | glucosyl |
| 408 | glucosyl | glucosyl | glucosyl | mannosyl |
| 409 | glucosyl | glucosyl | glucosyl | galactosyl |
| 410 | glucosyl | glucosyl | glucosyl | COCH$_3$ |
| 411 | glucosyl | glucosyl | glucosyl | COC$_3$H$_7$-i |
| 412 | glucosyl | glucosyl | glucosyl | COC$_{17}$H$_{35}$-n |
| 413 | glucosyl | glucosyl | glucosyl | COC$_{16}$H$_{33}$-n |
| 414 | glucosyl | glucosyl | glucosyl | COC$_{18}$H$_{37}$-n |
| 415 | glucosyl | glucosyl | glucosyl | CO(CH$_2$)$_7$CH=CHC$_6$H$_{13}$-n |
| 416 | glucosyl | glucosyl | glucosyl | COCH=CH$_2$ |
| 417 | glucosyl | glucosyl | glucosyl | COCH$_2$CH=CH$_2$ |
| 418 | COC$_{16}$H$_{33}$-n | COC$_{16}$H$_{33}$-n | COC$_{16}$H$_{33}$-n | SO$_3$H |
| 419 | COC$_{16}$H$_{33}$-n | COC$_{16}$H$_{33}$-n | COC$_{16}$H$_{33}$-n | PO$_3$H$_2$ |
| 420 | COC$_{16}$H$_{33}$-n | COC$_{16}$H$_{33}$-n | COC$_{16}$H$_{33}$-n | glucosyl |
| 421 | COC$_{16}$H$_{33}$-n | COC$_{16}$H$_{33}$-n | COC$_{16}$H$_{33}$-n | mannosyl |
| 422 | COC$_{16}$H$_{33}$-n | COC$_{16}$H$_{33}$-n | COC$_{16}$H$_{33}$-n | galactosyl |
| 423 | COC$_{16}$H$_{33}$-n | COC$_{16}$H$_{33}$-n | COC$_{16}$H$_{33}$-n | COCH$_3$ |
| 424 | COC$_{16}$H$_{33}$-n | COC$_{16}$H$_{33}$-n | COC$_{16}$H$_{33}$-n | COC$_3$H$_7$-i |
| 425 | COC$_{16}$H$_{33}$-n | COC$_{16}$H$_{33}$-n | COC$_{16}$H$_{33}$-n | COC$_{17}$H$_{35}$-n |
| 426 | COC$_{16}$H$_{33}$-n | COC$_{16}$H$_{33}$-n | COC$_{16}$H$_{33}$-n | COC$_{16}$H$_{33}$-n |
| 427 | COC$_{16}$H$_{33}$-n | COC$_{16}$H$_{33}$-n | COC$_{16}$H$_{33}$-n | COC$_{18}$H$_{37}$-n |
| 428 | COC$_{16}$H$_{33}$-n | COC$_{16}$H$_{33}$-n | COC$_{16}$H$_{33}$-n | CO(CH$_2$)$_7$CH=CHC$_6$H$_{13}$-n |
| 429 | COC$_{16}$H$_{33}$-n | COC$_{16}$H$_{33}$-n | COC$_{16}$H$_{33}$-n | COCH=CH$_2$ |
| 430 | COC$_{16}$H$_{33}$-n | COC$_{16}$H$_{33}$-n | COC$_{16}$H$_{33}$-n | COCH$_2$CH=CH$_2$ |
| 431 | CO(CH$_2$)$_7$CH=CHC$_6$H$_{13}$-n | CO(CH$_2$)$_7$CH=CHC$_6$H$_{13}$-n | CO(CH$_2$)$_7$CH=CHC$_6$H$_{13}$-n | SO$_3$H |
| 432 | CO(CH$_2$)$_7$CH=CHC$_6$H$_{13}$-n | CO(CH$_2$)$_7$CH=CHC$_6$H$_{13}$-n | CO(CH$_2$)$_7$CH=CHC$_6$H$_{13}$-n | PO$_3$H$_2$ |
| 433 | CO(CH$_2$)$_7$CH=CHC$_6$H$_{13}$-n | CO(CH$_2$)$_7$CH=CHC$_6$H$_{13}$-n | CO(CH$_2$)$_7$CH=CHC$_6$H$_{13}$-n | glucosyl |
| 434 | CO(CH$_2$)$_7$CH=CHC$_6$H$_{13}$-n | CO(CH$_2$)$_7$CH=CHC$_6$H$_{13}$-n | CO(CH$_2$)$_7$CH=CHC$_6$H$_{13}$-n | mannosyl |
| 435 | CO(CH$_2$)$_7$CH=CHC$_6$H$_{13}$-n | CO(CH$_2$)$_7$CH=CHC$_6$H$_{13}$-n | CO(CH$_2$)$_7$CH=CHC$_6$H$_{13}$-n | galactosyl |
| 436 | CO(CH$_2$)$_7$CH=CHC$_6$H$_{13}$-n | CO(CH$_2$)$_7$CH=CHC$_6$H$_{13}$-n | CO(CH$_2$)$_7$CH=CHC$_6$H$_{13}$-n | COCH$_3$ |
| 437 | CO(CH$_2$)$_7$CH=CHC$_6$H$_{13}$-n | CO(CH$_2$)$_7$CH=CHC$_6$H$_{13}$-n | CO(CH$_2$)$_7$CH=CHC$_6$H$_{13}$-n | COC$_3$H$_7$-i |
| 438 | CO(CH$_2$)$_7$CH=CHC$_6$H$_{13}$-n | CO(CH$_2$)$_7$CH=CHC$_6$H$_{13}$-n | CO(CH$_2$)$_7$CH=CHC$_6$H$_{13}$-n | COC$_{17}$H$_{35}$-n |
| 439 | CO(CH$_2$)$_7$CH=CHC$_6$H$_{13}$-n | CO(CH$_2$)$_7$CH=CHC$_6$H$_{13}$-n | CO(CH$_2$)$_7$CH=CHC$_6$H$_{13}$-n | COC$_{16}$H$_{33}$-n |
| 440 | CO(CH$_2$)$_7$CH=CHC$_6$H$_{13}$-n | CO(CH$_2$)$_7$CH=CHC$_6$H$_{13}$-n | CO(CH$_2$)$_7$CH=CHC$_6$H$_{13}$-n | COC$_{18}$H$_{37}$-n |
| 441 | CO(CH$_2$)$_7$CH=CHC$_6$H$_{13}$-n | CO(CH$_2$)$_7$CH=CHC$_6$H$_{13}$-n | CO(CH$_2$)$_7$CH=CHC$_6$H$_{13}$-n | CO(CH$_2$)$_7$CH=CHC$_6$H$_{13}$-n |
| 442 | CO(CH$_2$)$_7$CH=CHC$_6$H$_{13}$-n | CO(CH$_2$)$_7$CH=CHC$_6$H$_{13}$-n | CO(CH$_2$)$_7$CH=CHC$_6$H$_{13}$-n | COCH=CH$_2$ |
| 443 | CO(CH$_2$)$_7$CH=CHC$_6$H$_{13}$-n | CO(CH$_2$)$_7$CH=CHC$_6$H$_{13}$-n | CO(CH$_2$)$_7$CH=CHC$_6$H$_{13}$-n | COCH$_2$CH=CH$_2$ |

TABLE 2

| Compound # | $R^5$ | $R^6$ |
|---|---|---|
| 444 | H | H |
| 445 | $SO_3H$ | H |
| 446 | $PO_3H_2$ | H |
| 447 | glucosyl | H |
| 448 | mannosyl | H |
| 449 | galactosyl | H |
| 450 | $COCH_3$ | H |
| 451 | $COC_3H_7$-i | H |
| 452 | $COC_{17}H_{35}$-n | H |
| 453 | $COC_{16}H_{33}$-n | H |
| 454 | $COC_{18}H_{37}$-n | H |
| 455 | $CO(CH_2)_7CH=CHC_6H_{13}$-n | H |
| 456 | $COCH=CH_2$ | H |
| 457 | $COCH_2CH=CH_2$ | H |
| 458 | H | $SO_3H$ |
| 459 | H | $PO_3H_2$ |
| 460 | H | glucosyl |
| 461 | H | mannosyl |
| 462 | H | galactosyl |
| 463 | H | $COCH_3$ |
| 464 | H | $COC_3H_7$-i |
| 465 | H | $COC_{17}H_{35}$-n |
| 466 | H | $COC_{16}H_{33}$-n |
| 467 | H | $COC_{18}H_{37}$-n |
| 468 | H | $CO(CH_2)_7CH=CHC_6H_{13}$-n |
| 469 | H | $COCH=CH_2$ |
| 470 | H | $COCH_2CH=CH_2$ |
| 471 | $SO_3H$ | $SO_3H$ |
| 472 | $SO_3H$ | $PO_3H_2$ |
| 473 | $SO_3H$ | glucosyl |
| 474 | $SO_3H$ | mannosyl |
| 475 | $SO_3H$ | galactosyl |
| 476 | $SO_3H$ | $COCH_3$ |
| 477 | $SO_3H$ | $COC_3H_7$-i |
| 478 | $SO_3H$ | $COC_{17}H_{35}$-n |
| 479 | $SO_3H$ | $COC_{16}H_{33}$-n |
| 480 | $SO_3H$ | $COC_{18}H_{37}$-n |
| 481 | $SO_3H$ | $CO(CH_2)_7CH=CHC_6H_{13}$-n |
| 482 | $SO_3H$ | $COCH=CH_2$ |
| 483 | $SO_3H$ | $COCH_2CH=CH_2$ |
| 484 | $PO_3H_2$ | $SO_3H$ |
| 485 | $PO_3H_2$ | $PO_3H_2$ |
| 486 | $PO_3H_2$ | glucosyl |
| 487 | $PO_3H_2$ | mannosyl |
| 488 | $PO_3H_2$ | galactosyl |
| 489 | $PO_3H_2$ | $COCH_3$ |
| 490 | $PO_3H_2$ | $COC_3H_7$-i |
| 491 | $PO_3H_2$ | $COC_{17}H_{35}$-n |
| 492 | $PO_3H_2$ | $COC_{16}H_{33}$-n |
| 493 | $PO_3H_2$ | $COC_{18}H_{37}$-n |
| 494 | $PO_3H_2$ | $CO(CH_2)_7CH=CHC_6H_{13}$-n |
| 495 | $PO_3H_2$ | $COCH=CH_2$ |
| 496 | $PO_3H_2$ | $COCH_2CH=CH_2$ |
| 497 | glucosyl | $SO_3H$ |
| 498 | glucosyl | $PO_3H_2$ |
| 499 | glucosyl | glucosyl |
| 500 | glucosyl | mannosyl |
| 501 | glucosyl | galactosyl |
| 502 | glucosyl | $COCH_3$ |
| 503 | glucosyl | $COC_3H_7$-i |
| 504 | glucosyl | $COC_{17}H_{35}$-n |
| 505 | glucosyl | $COC_{16}H_{33}$-n |
| 506 | glucosyl | $COC_{18}H_{37}$-n |
| 507 | glucosyl | $CO(CH_2)_7CH=CHC_6H_{13}$-n |
| 508 | glucosyl | $COCH=CH_2$ |
| 509 | glucosyl | $COCH_2CH=CH_2$ |
| 510 | $COC_{16}H_{33}$-n | $SO_3H$ |
| 511 | $COC_{16}H_{33}$-n | $PO_3H_2$ |
| 512 | $COC_{16}H_{33}$-n | glucosyl |
| 513 | $COC_{16}H_{33}$-n | mannosyl |
| 514 | $COC_{16}H_{33}$-n | galactosyl |
| 515 | $COC_{16}H_{33}$-n | $COCH_3$ |
| 516 | $COC_{16}H_{33}$-n | $COC_3H_7$-i |
| 517 | $COC_{16}H_{33}$-n | $COC_{17}H_{35}$-n |
| 518 | $COC_{16}H_{33}$-n | $COC_{16}H_{33}$-n |
| 519 | $COC_{16}H_{33}$-n | $COC_{18}H_{37}$-n |
| 520 | $COC_{16}H_{33}$-n | $CO(CH_2)_7CH=CHC_6H_{13}$-n |
| 521 | $COC_{16}H_{33}$-n | $COCH=CH_2$ |
| 522 | $COC_{16}H_{33}$-n | $COCH_2CH=CH_2$ |
| 523 | $CO(CH_2)_7CH=CHC_6H_{13}$-n | $SO_3H$ |
| 524 | $CO(CH_2)_7CH=CHC_6H_{13}$-n | $PO_3H_2$ |
| 525 | $CO(CH_2)_7CH=CHC_6H_{13}$-n | glucosyl |
| 526 | $CO(CH_2)_7CH=CHC_6H_{13}$-n | mannosyl |
| 527 | $CO(CH_2)_7CH=CHC_6H_{13}$-n | galactosyl |
| 528 | $CO(CH_2)_7CH=CHC_6H_{13}$-n | $COCH_3$ |
| 529 | $CO(CH_2)_7CH=CHC_6H_{13}$-n | $COC_3H_7$-i |
| 530 | $CO(CH_2)_7CH=CHC_6H_{13}$-n | $COC_{17}H_{35}$-n |
| 531 | $CO(CH_2)_7CH=CHC_6H_{13}$-n | $COC_{16}H_{33}$-n |
| 532 | $CO(CH_2)_7CH=CHC_6H_{13}$-n | $COC_{18}H_{37}$-n |
| 533 | $CO(CH_2)_7CH=CHC_6H_{13}$-n | $CO(CH_2)_7CH=CHC_6H_{13}$-n |
| 534 | $CO(CH_2)_7CH=CHC_6H_{13}$-n | $COCH=CH_2$ |
| 535 | $CO(CH_2)_7CH=CHC_6H_{13}$-n | $COCH_2CH=CH_2$ |

Next, some examples of the formulations according to the present invention are shown. There is no particular limitation for mixing prescriptions for the formulations, and they are widely modifiable. The parts in the formulations of Examples represent parts by weight.

Formulation Example 1

Wettable Powder

| | |
|---|---|
| Substance (A) | 10 parts |
| Substance (B) | 10 parts |
| White carbon | 20 parts |
| Diatomaceous earth | 52 parts |
| Sodium alkyl sulfate | 8 parts |

The above materials are uniformly mixed, and finely ground to obtain a wettable powder.

Formulation Example 2

Emulsifiable Concentrate

| | |
|---|---|
| Substance (A) | 10 parts |
| Substance (B) | 10 parts |
| Xylene | 55 parts |
| Dimethylformamide | 15 parts |
| Polyoxyethylene phenyl ether | 10 parts |

The above materials are mixed, and dissolved to obtain an emulsifiable concentrate.

Formulation Example 3

Granule

| | |
|---|---|
| Substance (A) | 5 parts |
| Substance (B) | 5 parts |
| Talc | 37 parts |
| Clay | 36 parts |
| Bentonite | 10 parts |
| Sodium alkyl sulfate | 7 parts |

The above materials are uniformly mixed, finely ground, and then granulated to obtain a Granule.

Formulation Example 4

Flowable

| | |
|---|---|
| Substance (A) | 5 parts |
| Substance (B) | 5 parts |
| Polyoxyethylene aryl phenyl ether | 2 parts |
| Dialkyl sulfosuccinate sodium salt | 0.5 part |
| Glycerin | 5 parts |
| Xanthan gum | 0.3 part |
| Water | 82.2 parts |

The above materials are mixed and wet ground to obtain a flowable.

Formulation Example 5

Water Dispersible Granule

| | |
|---|---|
| Substance (A) | 15 parts |
| Substance (B) | 15 parts |
| Inorganic carrier | 70 parts |

The above materials are uniformly mixed, finely ground, and then granulated to obtain a water dispersible granule.

Test Example 1

Evaluation Test for Relief Effects of High Temperature Injury on *Arabidopsis thaliana*

N,N-dimethylformamide based solutions were prepared according to the formulas shown in Tables 3 to 6 to give the chemicals compositions 1 to 12 for the tests.

On each piece of water cultivation sponge, seeded were 10 seeds of *Arabidopsis thaliana* which had been subjected to surface disinfection, and allowed to grow for 14 days at 22° C. in 16 hours under a daylight condition and 8 hours under a dark condition to prepare test nursery plants.

The above chemicals composition was added dropwise at an amount of 100 µl to the plant foot of the above nursery plants, and allowed to grow for 2 days at 22° C. in 16 hours under a daylight condition and 8 hours under a dark condition.

Subsequently, the above nursery plants were allowed to stand at 35° C. for 1 hour under a dark condition, and then at 45° C. for 2 hours under a dark condition to cause high temperature injury to the nursery plants.

The above nursery plants were returned to the growth conditions of 22° C. for 16 hours under a daylight condition and 8 hours under a dark condition, and appearances of high temperature injury were investigated at the elapsed time of 4 days.

Evaluation was performed by six levels of high temperature injury indices of 0 (no disorder) to 5 (two or more withering true leaves). The high temperature injury relief percentages (%) as compared with the region treated with solvent DMF only (the chemicals composition 6) were computed by the following formula.

High temperature injury relief percents=((disorder index of region treated with solvent only)−(disorder index of each treatment region))/(disorder index of region treated with solvent only)×100

The results are shown in Tables 3 to 6.

TABLE 3

| | chemicals composition | | | | | |
|---|---|---|---|---|---|---|
| | 1 | 2 | 3 | 4 | 5 | 6 |
| Substance (A) [Conc. ppm] ascorbyl palmitate | 800 | 800 | 800 | 0 | 0 | 0 |
| Substance (B) [Conc. ppm] Pyraclostrobin | 80 | 40 | 0 | 80 | 40 | 0 |
| relief percents of high-temperature injury (%) | 75 | 69 | 30 | damage | 13 | 0 |

TABLE 4

| | chemicals composition | | | |
|---|---|---|---|---|
| | 3 | 6 | 7 | 8 |
| Substance (A) [Conc. ppm] ascorbyl palmitate | 800 | 0 | 800 | 0 |
| Substance (B) [Conc. ppm] Fluazinam | 0 | 0 | 50 | 50 |
| relief percents of high-temperature injury (%) | 30 | 0 | 70 | 11 |

TABLE 5

| | chemicals composition | | | |
|---|---|---|---|---|
| | 3 | 6 | 9 | 10 |
| Substance (A) [Conc. ppm] ascorbyl palmitate | 800 | 0 | 800 | 0 |
| Substance (B) [Conc. ppm] Kresoxim-methyl | 0 | 0 | 31 | 31 |
| relief percents of high-temperature injury (%) | 30 | 0 | 85 | 76 |

TABLE 6

| | chemicals composition | | | |
|---|---|---|---|---|
| | 3 | 6 | 11 | 12 |
| Substance (A) [Conc. ppm] ascorbyl palmitate | 800 | 0 | 800 | 0 |
| Substance (B) [Conc. ppm] Trifloxystrobin | 0 | 0 | 40 | 40 |
| relief percents of high-temperature injury (%) | 30 | 0 | 74 | 25 |

Test Example 2

Evaluation Test for Relief Effects of Low Temperature Injury on Eggplant

Eggplant (breed: Senryo 2 gou, 3 replications) grown up to the 4 to 6 leaf stage in a greenhouse was prepared.

A water dispersible granule of 30% ascorbyl palmitate and pyraclostrobin dissolved to 40% with N,N-dimethylformamide were diluted with tap water into a concentration described in Table 7, and the diluted solution was sprayed over the whole nursery plants in a sufficient amount. After air dried, they were allowed to grow for 1 day under conditions of 16 hours under a daylight condition at 18° C. and 8 hours under a dark condition at 13° C. Subsequently, they were allowed to grow for 15 days under conditions of 16 hours under a daylight condition at 13° C. and 8 hours under a dark condition at 8° C. A degree of disorder was investigated at the elapsed time of 15 days.

The area of a discolored portion in an expanded leaf after treatment was measured, and evaluated by 4 levels of disorder indices of 0 (with no color change), 1 (discolored up to ¼ of the whole), 2 (discolored up to ½ of the whole) and 3 (discolored to ½ or more of the whole), and injury relief percentages were computed by the following formula.

Low temperature injury relief percents=((disorder index of untreated region)−(disorder index of each treated region))/(disorder index of untreated region)×100

The results are shown in Table 7.

TABLE 7

|  | chemicals composition | | | |
| --- | --- | --- | --- | --- |
|  | 13 | 14 | 15 | 16 |
| Substance (A) [Conc. ppm] ascorbyl palmitate | 1000 | 0 | 0 | 1000 |
| Substance (B) [Conc. ppm] Pyraclostrobin | 0 | 50 | 0 | 50 |
| relief percents of low-temperature injury (%) | 13.0 | 13.0 | 0.0 | 71.2 |

Test Example 3

Evaluation Test for Relief Effects of High Temperature Injury on Tomato

Tomato (breed: Momotaro, 2 replications) grown up to the 4 leaf stage in a greenhouse was prepared.

A water dispersible granule of 30% ascorbyl palmitate and a commercially available agent containing the substance (B) as described in Table 8 were diluted with tap water into a concentration described in Table 8, and the diluted solution was sprayed over the whole nursery plants in a sufficient amount. After air dried, they were allowed to grow under cycle conditions of 16 hours under a daylight condition at 40° C. and 8 hours under a dark condition at 30° C. The degree of disorders was investigated at an elapsed time of 4 days after the spraying.

The degree of necrosis due to high temperature was evaluated by 11 levels of disorder indices from 0 (no necrosis) to 10 (withering to death). From this, the injury relief percentages were computed by the following formula.

Injury relief percent=((disorder index of region treated with solvent only)−(disorder index of each treated region))/(disorder index of region treated with solvent only)×100

The results are shown in Table 8.

TABLE 8

|  | Chemicals composition (conc. of each chemicals) | relief percents of injury (%) |
| --- | --- | --- |
| substance (A) | ascorbyl palmitate (600 ppm) | 40 |
| substance (B) | Thiophanate-methyl (467 ppm) | 40 |
| substance (A) substance (B) | ascorbyl palmitate (600 ppm) + Thiophanate-methyl (467 ppm) | 60 |
| substance (B) | Boscalid (333 ppm) | 40 |
| substance (A) substance (B) | ascorbyl palmitate (600 ppm) + Boscalid (333 ppm) | 60 |
| substance (B) | Cyflufenamid (17 ppm) + Triflumizole (75 ppm) | 40 |

TABLE 8-continued

|  | Chemicals composition (conc. of each chemicals) | relief percents of injury (%) |
| --- | --- | --- |
| substance (A) substance (B) | ascorbyl palmitate (600 ppm) + Cyflufenamid (17 ppm) + Triflumizole (75 ppm) | 60 |
| Untreated |  | 0 |

Test Example 4

Evaluation Test for Relief Effects of Strong Light Injury on Tomato

Tomato (breed: Reiyo, 2 replications) grown up to the two leaf stage in a greenhouse was prepared.

A water dispersible granule of 30% ascorbyl palmitate and pyraclostrobin dissolved to 40% with N,N-dimethylformamide were diluted with tap water into a concentration described in Table 9, and the diluted solution was sprayed over the whole nursery plant in a sufficient amount. After air dried, it was exposed to strong light under summer blazing sun. The degree of disorder was investigated at the elapsed time of 4 days after the spraying.

The degree of necrosis due to light effects was evaluated by 11 levels of disorder indices from 0 (no necrosis) to 10 (withering to death). From this, injury relief percentages were computed by the following formula.

Strong light injury relief percentage=((disorder index of untreated region)−(disorder index of each treated region))/(disorder index of untreated region)×100

The results are shown in Table 9.

TABLE 9

|  | chemicals composition | | | |
| --- | --- | --- | --- | --- |
|  | 13 | 14 | 15 | 16 |
| Substance (A) [Conc. ppm] ascorbyl palmitate | 1000 | 0 | 0 | 1000 |
| Substance (B) [Conc. ppm] Pyraclostrobin | 0 | 50 | 0 | 50 |
| relief percents of strong light injury (%) | 50 | 40 | 0 | 80 |

Test Example 4

Evaluation Test for Relief Effects of Flood Injury on Cucumber

Cucumber (breed: Sagamihanjirohushinari, 2 replications) grown up to the two leaf stage in a greenhouse was prepared.

A water dispersible granule of 30% ascorbyl palmitate and pyraclostrobin dissolved to 40% with N,N-dimethylformamide were diluted with tap water into a concentration described in Table 10, and the diluted solution was sprayed in a sufficient amount. They were subjected to flood conditions up to immediately below the cotyledon from the elapsed time of 2 days after the spraying, and the raw weights of an above ground part and a root part of cucumber were each measured at the elapsed time of 11 days after the spraying. From this, injury relief percentages were computed by the following formula.

Flood injury relief percentage=((raw weight of each treatment region)−(raw weight of untreated region))/(raw weight of untreated region)×100

The results are shown in Table 10.

TABLE 10

| | chemicals composition | | | |
|---|---|---|---|---|
| | 13 | 14 | 15 | 16 |
| Substance (A) [Conc. ppm] ascorbyl palmitate | 1000 | 0 | 0 | 1000 |
| Substance (B) [Conc. ppm] Pyraclostrobin | 0 | 50 | 0 | 50 |
| relief percents of flood injury in stem and leaf (%) | 31.9 | 61.7 | 0.0 | 83.0 |
| relief percents of flood injury in root (%) | 41.5 | 39.0 | 0.0 | 78.0 |

Test Example 5

Evaluation Test for Relief Effects of Flood Injury on Soybean

Soybean (breed: Enrei, 2 replications) grown up to the two leaf stage in a greenhouse was prepared.

A water dispersible granule) of 30% ascorbyl palmitate and pyraclostrobin dissolved to 40% with N,N-dimethylformamide were diluted with tap water into a concentration described in Table 11, and the diluted solution was sprayed in a sufficient amount. They were subjected to flood conditions up to immediately below the cotyledon from the elapsed time of 2 days after the spraying, and the raw weights of an above ground part and a root part of soybean were each measured at the elapsed time of 11 days after the spraying. From this, injury relief percentages were computed by the following formula.

Flood injury relief percentage=((raw weight of each treatment region)−(raw weight of untreated region))/(raw weight of untreated region)×100

The results are shown in Table 11.

TABLE 11

| | chemicals composition | | | |
|---|---|---|---|---|
| | 13 | 14 | 15 | 16 |
| Substance (A) [Conc. ppm] ascorbyl palmitate | 1000 | 0 | 0 | 1000 |
| Substance (B) [Conc. ppm] Pyraclostrobin | 0 | 50 | 0 | 50 |
| relief percents of flood injury in stem and leaf (%) | 2.8 | 0.0 | 0.0 | 16.7 |
| relief percents of flood injury in root (%) | 20.4 | 3.2 | 0.0 | 22.6 |

Test Example 6

Evaluation Test for Relief Effects of Acidity Problem on Cucumber

Cucumber (breed: Sagamihanjirohushinari, 2 replications) hydroponically grown up to the two leaf stage in a 100 ml flask was prepared.

A water dispersible granule of 30% ascorbyl palmitate and pyraclostrobin dissolved to 40% with N,N-dimethylformamide were diluted with tap water into a concentration described in Table 12, and the diluted solution was sprayed over the whole nursery plants in a sufficient amount. The water culture medium was adjusted to pH 4 with 1 N hydrochloric acid at the elapsed time of 2 days after the spraying, and the above cucumber was continuously allowed to grow hydroponically. Leaf stage of the cucumber was investigated at the elapsed time of 17 days after the spraying. From this, problem relief percentages were computed by the following formula.

Acidity problem relief percentage=((leaf stage of each treatment region)−(leaf stage of untreated region))/(leaf stage of untreated region)×100

The results are shown in Table 12.

TABLE 12

| | chemicals composition | | | |
|---|---|---|---|---|
| | 13 | 14 | 15 | 16 |
| Substance (A) [Conc. ppm] ascorbyl palmitate | 1000 | 0 | 0 | 1000 |
| Substance (B) [Conc. ppm] Pyraclostrobin | 0 | 50 | 0 | 50 |
| relief percents of acidity problem (%) | 15.6 | 15.6 | 0.0 | 32.8 |

Test Example 7

Evaluation Test for Relief Effects of Acidity Problem on Soybean

Soybean (breed: Enrei, 2 replications) hydroponically grown up to the two leaf stage in a 100 ml flask was prepared.

A water dispersible granule of 30% ascorbyl palmitate and pyraclostrobin dissolved to 40% with N,N-dimethylformamide were diluted with tap water to a concentration described in Table 13, and the diluted solution was sprayed over the whole nursery plants in a sufficient amount. The water culture medium was adjusted to pH 4 with 1 N hydrochloric acid at the elapsed time of 2 days after the spraying, and the above soybean was continuously allowed to grow hydroponically. Disorder of the above soybean was investigated at the elapsed time of 11 days after the spraying.

The degree of necrosis was evaluated by 11 levels of disorder indices from 0 (no necrosis) to 10 (withering to death). From this, problem relief percentages were computed by the following formula.

Acidity problem relief percentage=((disorder index of untreated region)−(disorder index of each treated region))/(disorder index of untreated region)×100

The results are shown in Table 13.

TABLE 13

| | chemicals composition | | | |
|---|---|---|---|---|
| | 13 | 14 | 15 | 16 |
| Substance (A) [Conc. ppm] ascorbyl palmitate | 1000 | 0 | 0 | 1000 |
| Substance (B) [Conc. ppm] Pyraclostrobin | 0 | 50 | 0 | 50 |
| relief percents of acidity problem (%) | 43.8 | 12.5 | 0.0 | 56.3 |

Test Example 8

Evaluation Test for Relief Effects of Salt Injury on Cucumber

Cucumber (breed: Sagamihanjiro, 2 replications) hydroponically grown up to the 1.5 leaf stage in a greenhouse was prepared.

A water dispersible granule of 30% ascorbyl palmitate and a commercially available product containing the substance (B) described in Table 14 were diluted with tap water into a concentration described in Table 14, and the diluted solution was sprayed over the nursery plats in a sufficient amount. After air dried, they were cultivated in a greenhouse with normal irrigation. Irrigation was changed to 0.1% aqueous sodium chloride solution at the elapsed time of 3 days after the spraying, and cultivated. The raw weight of an above ground part was measured at the elapsed time of 20 days after the spraying. From this, injury relief percentages were computed by the following formula. Note that a cultivation under normal irrigation for 20 days without chemical spraying is denoted as the normal irrigation region.

Injury relief percentage=((raw weight of each treatment region)−(raw weight of untreated region))/((raw weight of normal irrigation region)−(raw weight of untreated region)×100

The results are shown in Table 14.

TABLE 14

| Chemicals composition (conc. of each chemicals) | | relief percents of injury (%) |
|---|---|---|
| substance (A) | ascorbyl palmitate (600 ppm) | 53 |
| substance (B) | Imidacloprid (50 ppm) | 33 |
| substance (A) substance (B) | ascorbyl palmitate (600 ppm) + Imidacloprid (50 ppm) | 100 |
| substance (B) | Pymetrozine (100 ppm) | 53 |
| substance (A) substance (B) | ascorbyl palmitate (600 ppm) + Pymetrozine (100 ppm) | 86 |
| substance (B) | cyenopyrafen (150 ppm) | 51 |
| substance (A) substance (B) | ascorbyl palmitate (600 ppm) + cyenopyrafen (150 ppm) | 105 |
| substance (B) | Pyraclostrobin (50 ppm) | 77 |
| substance (A) substance (B) | ascorbyl palmitate (600 ppm) + Pyraclostrobin (50 ppm) | 153 |
| Untreated | | 0 |
| normal irrigation | | 100 |

Test Example 9

Evaluation Test for Relief Effects of Salt Injury on Cucumber

Cucumber (breed: Sagamihanjirohushinari, 2 replications) hydroponically grown up to the two leaf stage in a greenhouse was prepared.

A water dispersible granule of 30% ascorbyl palmitate and pyraclostrobin adjusted to 40% with N,N-dimethylformamide were diluted with tap water into a concentration described in Table 15, and the diluted solution was sprayed over the whole nursery plants in a sufficient amount. After air dried, they were cultivated in a greenhouse with normal irrigation. The irrigation conditions were changed to 0.1% aqueous sodium chloride solution in 2 cm depth at the elapsed time of 2 days, and cultivated. The raw weights of an above ground part and a root part were each measured at the elapsed time of 11 days after the spraying. From this, injury relief percentages were computed by the following formula.

Salt injury relief percentage=((raw weight of each treatment region)−(raw weight of untreated region))/(raw weight of untreated region)×100

The results are shown in Table 15.

TABLE 15

| | chemicals composition | | | |
|---|---|---|---|---|
| | 13 | 14 | 15 | 16 |
| Substance (A) [Conc. ppm] ascorbyl palmitate | 1000 | 0 | 0 | 1000 |
| Substance (B) [Conc. ppm] Pyraclostrobin | 0 | 50 | 0 | 50 |
| relief percents of salt injury in aerial part (%) | 8.8 | 45.6 | 0.0 | 50.0 |
| relief percents of salt injury in root (%) | 16.0 | 20.0 | 0.0 | 40.0 |

Test Example 10

Evaluation Test for Relief Effects of Salt Injury on Soybean

Soybean (breed: Enrei, 2 replications) hydroponically grown up to the two leaf stage in a greenhouse was prepared.

A water dispersible granule t of 30% ascorbyl palmitate and pyraclostrobin adjusted to 40% with N,N-dimethylformamide were diluted with tap water into a concentration described in Table 16, and the diluted solution was sprayed over the whole nursery plants in a sufficient amount. After air dried, they were cultivated in a greenhouse with normal irrigation. The irrigation conditions were changed to 0.1% aqueous sodium chloride solution in 2 cm depth at the elapsed time of 2 days, and cultivated. The raw weights of an above ground part and a root part were each measured at the elapsed time of 11 days after the spraying. From this, injury relief percentages were computed by the following formula.

Injury relief percentage=((raw weight of each treatment region)−(raw weight of untreated region))/(raw weight of untreated region)×100

The results are shown in Table 16.

TABLE 16

| | chemicals composition | | | |
|---|---|---|---|---|
| | 13 | 14 | 15 | 16 |
| Substance (A) [Conc. ppm] ascorbyl palmitate | 1000 | 0 | 0 | 1000 |
| Substance (B) [Conc. ppm] Pyraclostrobin | 0 | 50 | 0 | 50 |
| relief percents of salt injury in aerial part (%) | 20.4 | 3.2 | 0.0 | 22.6 |
| relief percents of salt injury in root (%) | 22.2 | 2.5 | 0.0 | 33.3 |

Test Example 11

Evaluation Test for Relief Effects of Phytotoxicity on Tomato

N,N-dimethylformamide based solutions were prepared according to the formulas shown in Table 17 to obtain chemicals compositions for the tests.

Tomato nursery plants (breed: Momotaro) grown up to the 4 leaf stage in a greenhouse were prepared.

The above chemicals composition was sprayed to the stem and leaf parts of the above tomato nursery plants in a sufficient amount. After air dried, they were cultivated under the average temperature and humidity conditions on March in Japan. Phytotoxicity such as a degree of leaf necrisis and growth inhibition was investigated at the elapsed time of 7 days after the spraying.

Phytotoxicity was evaluated by 11 levels of phytotoxicity indices of 0 (with no disorder) to 10 (withering to death). Phytotoxicity relief percentages as compared with the region treated with solvent DMF only were computed by the following formula.

Phytotoxicity relief percentage=(Phytotoxicity index of region treated with solvent only)−(Phytotoxicity index of each treated region))/(Phytotoxicity index of region treated with solvent only)×100

The results are shown in Table 17.

TABLE 17

| | Chemicals composition | | | | | | | |
|---|---|---|---|---|---|---|---|---|
| | 17 | 18 | 19 | 20 | 21 | 22 | 23 | 24 |
| Substance (A) [Conc. ppm] | | | | | | | | |
| ascorbyl palmitate | 800 | 800 | 0 | 0 | 800 | 800 | 0 | 0 |
| Substance (B) [Conc. ppm] | | | | | | | | |
| Fluazinam | 200 | 100 | 200 | 100 | 0 | 0 | 0 | 0 |
| Azoxystrobin | 0 | 0 | 0 | 0 | 200 | 100 | 200 | 100 |
| phytotoxicity index | 4 | 2 | 6 | 6 | 4 | 3 | 6 | 5 |
| relief percents of damage (%) | 33 | 67 | 0 | 0 | 33 | 40 | 0 | 0 |

Test Example 12

Tests for Relief Effects of Disease Stress on Rice Plant

Nursery plants of rice (breed: Koshihikari, 10 replications) were prepared. A water dispersible granule of 30% ascorbyl palmitate and pyraclostrobin adjusted to 5% with N,N-dimethylformamide were diluted with tap water into a concentration described in Table 18, and the diluted solution was sprayed over the whole nursery plants in a sufficient amount. They were inoculated with *Magnaporthe grisea* at the elapsed time of 1 day after the air drying. The number of rice blast lesion spots was investigated at the elapsed time of 11 days after the inoculation. From this, preventive values were computed by the following formula.

Preventive value=((number of lesion spots in untreated region)−(number of lesion spots in each treated region))/(number of lesion spots in untreated region)×100

The results are shown in Table 18.

TABLE 18

| | chemicals composition | | | |
|---|---|---|---|---|
| | 25 | 26 | 27 | 28 |
| Substance (A) [Conc. ppm] ascorbyl palmitate | 50 | 0 | 0 | 50 |

TABLE 18-continued

| | chemicals composition | | | |
|---|---|---|---|---|
| | 25 | 26 | 27 | 28 |
| Substance (B) [Conc. ppm] Pyraclostrobin | 0 | 5 | 0 | 5 |
| number of lesion | 30 | 10 | 33 | 6 |
| preventive value (%) | 9 | 70 | 0 | 82 |

Test Example 13

Tests for Relief Effects of Disease Stress on Rice Plant

Nursery plants of rice (breed: Koshihikari, the 4 leaf stage, 1 replication of 5 plants) were prepared. A commercially available agent containing 96 mg of probenazole was applied to a water surface. A water dispersible granule of 30% ascorbyl palmitate was diluted with tap water into a concentration described in Table 19, and the diluted solution was sprayed over the whole nursery plants in a sufficient amount at the elapsed time of 2 days after the application on the water surface. They were inoculated with *Magnaporthe grisea* at the elapsed time of 1 day after the air drying. The area of rice blast spots was investigated at the elapsed time of 11 days after the inoculation. Evaluation was performed by 5 levels of 0: no disease onset, 1: a disease onset area of less than 25%, 2: a disease onset area of not less than 25% and less than 50%, 3: a disease onset area of not less than 50% and less than 75%, 4: a disease onset area of not less than 75% as a disease onset index per plant. From this, preventive values were computed by the following formula.

Preventive value=((disease onset index of untreated region)−(disease onset index of each treated region))/(disease onset index of untreated region)×100

The results are shown in Table 19.

TABLE 19

| | Chemicals composition | | | | | | | |
|---|---|---|---|---|---|---|---|---|
| | 29 | 30 | 31 | 32 | 33 | 34 | 35 | 36 |
| Substance (A) [Conc. ppm] | | | | | | | | |
| ascorbyl palmitate | 1600 | 400 | 100 | 0 | 0 | 1600 | 400 | 100 |
| Substance (B) [appl. amount, mg] | | | | | | | | |
| Probenazole | 0 | 0 | 0 | 96 | 0 | 96 | 96 | 96 |
| onset index (mean per plant) | 1.4 | 2.6 | 2.6 | 1.6 | 2.8 | 0.4 | 0.8 | 1.2 |
| preventive value (%) | 50 | 7 | 7 | 43 | 0 | 86 | 71 | 57 |

The invention claimed is:

1. A chemicals composition for reducing stress on a plant wherein the composition comprises
at least one substance (A) selected from the group consisting of
compounds represented by Formula (I):

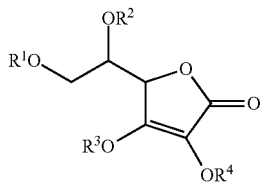

in Formula (I), $R^1$ to $R^4$ each independently represents a hydrogen atom, —$SO_3H$, —$PO_3H_2$, a glycosyl group or —$COR^{11}$, $R^{11}$ represents a C1 to C30 alkyl group, a C2 to C30 alkenyl group, a C1 to C30 alkyl group having a substituent or a C2 to C30 alkenyl group having a substituent, the substituent in the C1 to C30 alkyl group or the C2 to C30 alkenyl group being a hydroxyl group; a mercapto group; an amino group; a nitro group; a halogen atom; an alkoxy group; an aryloxy group; a fluoromethoxy group, a difluoromethoxy group, a trifluoromethoxy group, a 2-chloroethoxy group, a 2,2,2-trichloroethoxy group, a haloalkoxy group; an arylthio group; an alkylamino group; an arylamino group; or a cyano group,
compounds represented by Formula (II):

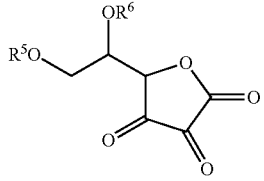

in Formula (II), $R^5$ and $R^6$ each independently represents a hydrogen atom, —$SO_3H$, —$PO_3H_2$, a glycosyl group or —$COR^{11}$,
$R^{11}$ represents a C1 to C30 alkyl group, a C2 to C30 alkenyl group, a C1 to C30 alkyl group having a substituent or a C2 to C30 alkenyl group having a substituent, the substituent in the C1 to C30 alkyl group or the C2 to C30 alkenyl group being a hydroxyl group; a mercapto group; an amino group; a nitro group; a halogen atom; an alkoxy group; an aryloxy group; a fluoromethoxy group, a difluoromethoxy group, a trifluoromethoxy group, a 2-chloroethoxy group, a 2,2,2-trichloroethoxy group, a haloalkoxy group; an arylthio group; an alkylamino group; an arylamino group; or a cyano group, and salts thereof; and
a substance (B) which affects a physiological function of the plant, the substance (B) being respiratory inhibitor.

2. The composition according to claim 1, wherein the substance (B) is a strobilurin compound.

3. The composition according to claim 1, wherein the substance (A) is a compound represented by Formula (I), provided that $R^1$ to $R^4$ are each not simultaneously a hydrogen atom, or a salt thereof.

4. The composition according to claim 1, wherein the substance (A) is a compound represented by Formula (I), provided that at least one of $R^1$ to $R^4$ represents —$COR^{11}$, and
$R^{11}$ represents a C12 to C30 alkyl group, a C12 to C30 alkenyl group, a C12 to C30 alkyl group having a substituent or a C12 to C30 alkenyl group having a substituent, the substituent in the C12 to C30 alkyl group or the C12 to C30 alkenyl group being a hydroxyl group; a mercapto group; an amino group; a nitro group; a halogen atom; an alkoxy group; an aryloxy group; a fluoromethoxy group, a difluoromethoxy group, a trifluoromethoxy group, a 2-chloroethoxy group, a 2,2,2-trichloroethoxy group, a haloalkoxy group; an arylthio group; an alkylamino group; an arylamino group; or a cyano group, or a salt thereof.

5. The composition according to claim 1, wherein the substance (A) is a compound represented by Formula (I), provided that $R^1$ to $R^4$ are each independently a hydrogen atom or —$COR^{11}$, and at least one of $R^1$ to $R^4$ represents —$COR^{11}$,
$R^{11}$ represents a C1 to C30 alkyl group, a C2 to C30 alkenyl group, a C1 to C30 alkyl group having a substituent or a C2 to C30 alkenyl group having a substituent, the substituent in the C1 to C30 alkyl group, or the C2 to C30 alkenyl group being a hydroxyl group; a mercapto group; an amino group; a nitro group; a halogen atom; an alkoxy group; an aryloxy group; a fluoromethoxy group, a difluoromethoxy group, a trifluoromethoxy group, a 2-chloroethoxy group, a 2,2,2-trichloroethoxy group, a haloalkoxy group; an arylthio group; an alkylamino group; an arylamino group; or a cyano group,
$R^{11}$ in at least one of —$COR^{11}$ represents a C12 to C30 alkyl group, a C12 to C30 alkenyl group, a C12 to C30 alkyl group having a substituent or a C12 to C30 alkenyl group having a substituent, the substituent in the C12 to C30 alkyl group or the C12 to C30 alkenyl group being a hydroxyl group; a mercapto group; an amino group; a nitro group; a halogen atom; an alkoxy group; an aryloxy group; a fluoromethoxy group, a difluoromethoxy group, a trifluoromethoxy group, a 2-chloroethoxy group, a 2,2,2-trichloroethoxy group, a haloalkoxy group; an arylthio group; an alkylamino group; an arylamino group; or a cyano group, or a salt thereof.

6. A method of reducing stress on a plant, wherein the method comprises applying the composition according to claim 1 to the plant.

7. The method according to claim 6, wherein the stress is at least one of biological stress due to plant viruses, phytopathogenic bacteria, phytopathogenic filamentous fungi, agricultural pests or weeds; or physical or chemical stress due to high temperature, low temperature, high illuminance, low illuminance, excessive humidity, dryness, salt, acidity, agricultural chemicals, fertilizers, surfactants, or heavy metals.

* * * * *